(12) United States Patent
Sugito

(10) Patent No.: US 8,092,441 B2
(45) Date of Patent: Jan. 10, 2012

(54) DISPOSABLE WEARING ARTICLE

(75) Inventor: Tomoko Sugito, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 109 days.

(21) Appl. No.: 12/750,479

(22) Filed: Mar. 30, 2010

(65) Prior Publication Data

US 2010/0185169 A1    Jul. 22, 2010

Related U.S. Application Data

(62) Division of application No. 11/169,662, filed on Jun. 30, 2005, now Pat. No. 7,758,559.

(30) Foreign Application Priority Data

Jun. 30, 2004    (JP) ................................. 2004-194187

(51) Int. Cl.
*A61F 13/15* (2006.01)

(52) U.S. Cl. ........................ 604/389; 604/390; 604/367

(58) Field of Classification Search ............. 604/385.01, 604/385.24–385.3, 386–390, 367
See application file for complete search history.

(56) References Cited

U.S. PATENT DOCUMENTS

| 5,722,969 | A | 3/1998 | Ito et al. |
| 6,511,466 | B1 | 1/2003 | Nagami et al. |
| 2004/0243091 | A1 | 12/2004 | Mitsui et al. |

FOREIGN PATENT DOCUMENTS

| EP | 0 974 326 A1 | 1/2000 |
| EP | 1 166 737 | 1/2002 |
| JP | 1995-88133 | 4/1995 |
| JP | 2000-080337 | 3/2000 |
| WO | 00/40193 | 7/2000 |
| WO | 01/13852 A1 | 3/2001 |
| WO | 01/87206 | 11/2001 |
| WO | 03/082172 | 10/2003 |

OTHER PUBLICATIONS

European Search Report of International Application No. 05765336.2-2124/01764068 PCT/JP2005012125 mailed Jun. 29, 2009.

*Primary Examiner* — Michele Kidwell

(74) *Attorney, Agent, or Firm* — Lowe, Hauptman, Ham & Berner, LLP

(57) ABSTRACT

A disposable wearing article has longitudinally extending side edges of a front waist region. The side edges are defined by a pair of hydrophobic fibrous nonwoven fabric layers having mutually opposed surfaces tightly bonded to each other. Fastening zones are formed by an adhesive applied on longitudinally extending side edges of the rear waist region. Landing zones are formed from plastic filmstrip tightly bonded to the side edges of the front waist region.

13 Claims, 17 Drawing Sheets

DISPOSABLE WEARING ARTICLE

This is a Divisional Application of U.S. application Ser. No. 11,169,662 filed on Jun. 30, 2005, which is based on, and claims priority from Japan Application Number 2004-194187 filed Jun. 30, 2004. The disclosures of all above applications are hereby incorporated by reference herein in their entirety.

BACKGROUND OF THE INVENTION

This invention relates to a disposable wearing article for absorption and containment of body fluid.

There have already been proposed disposable wearing articles defining a front waist region, a rear waist regions and a crotch region extending between these waist regions and comprising a liquid-pervious topsheet, a liquid-impervious backsheet and a liquid-absorbent core interposed between these sheets and extending between the front and rear waist regions. The transverse side edges of the rear waist region is formed on inner surfaces thereof with adhesive zones and protective release zones extending in a longitudinal direction. One of the diapers is disclosed, for example, in Japanese Unexamined Patent Application No. 1995-88133, hereinafter referred to as "Reference"). Before actual use of the article, the adhesive zones is maintained to be removably bonded to the protective release zones.

To put the article on a wearer, the adhesive zones may be peeled off from the respective release zones, the transverse side edges of the rear waist region may be put on the outer surface of the front waist region and the adhesive zones are bonded to the outer surface of the front waist region (i.e., the outer surface of the backsheet) to connect the front waist region with the rear waist region. Thereupon the article is formed with a waist-hole and a pair of leg-holes. Each of the adhesive zones has a predetermined tack strength relative to the backsheet. This tack strength is sufficient to avoid an anxiety that the backsheet might be torn as the adhesive zones are peeled off from the outer surface of the front waist region and/or the adhesive zones might be unintentionally peeled off from the backsheet during use of the article.

Generally, one of the reasons why a tack strength of the adhesive zones decreases is that an adhesive material of the adhesive zones is set. To restore a desired tack strength of the adhesive material having been set, the adhesive material may be warmed to soften.

In the case of the article disclosed in Reference, the liquid-absorbent core underlies landing zones of the front waist region to which the adhesive zones are bonded. The presence of this core makes it difficult for body warmth from the wearer to transfer the adhesive zones bonded to the front waist region and makes it impossible for the body warmth of the wearer to warm the adhesive material of the adhesive zones to be softened. Consequentially, it is impossible for the adhesive material to a restore a desirable tack strength and there is likely that a peel strength of the adhesive zones to the landing zones would be deteriorated.

SUMMARY OF THE INVENTION

It is an object of this invention to provide a disposable wearing article improved so that the deterioration of the aforesaid peel strength can be prevented.

This invention includes a first aspect and a second aspect.

The first and second aspects of this invention is respectively directed to a disposable wearing article comprising: a first waist region; a second waist region; a crotch region between the first and second waist regions; transversely extending ends of the first and second waist regions; longitudinally extending side edges between the transversely extending ends; fastening zones provided on inner surfaces of the longitudinally extending side edges of the first waist region; landing zones provided on outer surfaces of the second waist region so that said fastening zones are releasably fastened on the landing zones; the longitudinal extending side edges of the second waist region comprising plural sheets having mutually opposed surfaces tightly bonded to each other.

The first aspect of this invention further comprises: the fastening zones each being formed from an adhesive layer applied with an adhesive material on the inner surface of the longitudinally extending side edge of the first waist region, the adhesive layer being softened by being warmed, and the landing zones each being formed from one of a plastic film strip tightly bonded to the outer surface of the longitudinally extending side edge of the second waist region and an adhesive layer applied with an adhesive material on the outer surface of the longitudinally extending side edge of the second waist region.

The second aspect of this invention further comprises: the fastening zones each being formed from one of a plastic film strip tightly bonded to the inner surface of the longitudinally extending side edge of the first waist region and an adhesive layer applied with an adhesive material on the inner surface of the longitudinally extending side edge of the first waist region; and the landing zones each being formed from an adhesive layer applied with an adhesive material on the outer surface of the longitudinally extending side edge of the second waist region, the adhesive layer being softened by being warmed.

The first and second aspects of this invention may respectively include preferred embodiments as follows:

Waist elastic members extending in a transverse direction are contractibly attached to the transversely extending ends of the first and second waist regions, at least the end of the second waist region; leg elastic members extending in the longitudinal direction are contractibly attached to the crotch region along the longitudinally extending side edges thereof; a plurality of auxiliary elastic members spaced one from another in the longitudinal direction by a predetermined dimension and extending in the transverse direction are contractibly attached to the article between the waist elastic members at least in the second waist region of the first and second waist regions and the leg elastic members; and lengthwise ends of the waist elastic members, lengthwise end of the leg elastic members and lengthwise ends of the auxiliary elastic members extend toward the longitudinally extending side edges of the second waist region wherein these ends are interposed between the sheets and tightly bonded to the mutually opposed surfaces of the sheets.

The lengthwise ends of the auxiliary elastic members terminate in a vicinity of mutually opposed inner side edges of the landing zones.

The lengthwise ends of the waist elastic members as well as the lengthwise end of the leg elastic members terminate in a vicinity of the mutually opposed inner side edges of the landing zones.

The adhesive layer has a thickness dimension in a range of 5 to 100 μm.

A peel strength between the fastening zones and the landing zones in a state bonded to each other at room temperature is in a range of 3 to 8 N/25 mm, the peel strength one hour after the fastening zones have been bonded to the landing zones is in a range of 5 to 11 N/25 mm and the peel strength three hours after the fastening zones have been bonded to the landing zones is in a range of 6 to 12 N/25 mm, respectively at a temperature of 36 to 40° C.

In the disposable wearing article according to this invention, the longitudinally extending side edges of the second waist region are formed from a pair of sheets tightly bonded together with no clearance left therebetween. Consequentially, the longitudinally extending side edges of the second waist region allow to be warmed by body warmth of the wearer transferred through the side edges of the second waist region when worn and thereby to be softened. Consequentially, the tack strength of the adhesive layer deteriorated due to setting thereof can be restored while a temperature of the adhesive layer is maintained at a temperature near body warmth of the wearer and thereby the tack strength can be prevented from deteriorating due to setting of the adhesive layer under a low temperature. In this way, the peel strength between the fastening zones and the length zones can be prevented from deteriorating.

The article wherein the lengthwise ends of the waist elastic members, the lengthwise end of the leg elastic members and the lengthwise ends of the auxiliary elastic members extend toward the longitudinally extending side edges of the second waist region and are interposed between the sheets forming the longitudinally extending side edges of the second waist region and tightly bonded to the mutually opposed surfaces of these sheets ensure the body warmth of the wearer to be reliably transferred to the adhesive layer through the longitudinally extending side edges of the second waist region, since no clearance is left between mutually opposed surfaces of the sheets as well as between these sheets and the lengthwise ends of the elastic members.

In the case of the article wherein the lengthwise ends of the auxiliary elastic members terminate in the vicinity of the mutually opposed inner side edges of the landing zones, even if such elastic members are present therein, body warmth of the wearer is reliably transferred to the adhesive layer.

In the case of the article wherein the lengthwise ends of the waist elastic members and the lengthwise end of the leg elastic members terminate in the vicinity of the mutually opposed inner side edges of the landing zones, even if such elastic members are present therein, body warmth of the wearer is reliably transferred to the adhesive layer.

With the article wherein the adhesive layer has a thickness dimension in a range of 5 to 100 μm, warming the adhesive layer's adhesive material is accelerated and thereby to accelerate restoration of the tack strength of the adhesive layer deteriorated due to setting thereof.

DETAILED DESCRIPTION OF THE PREFERRED EMBODIMENTS

Figure 1:
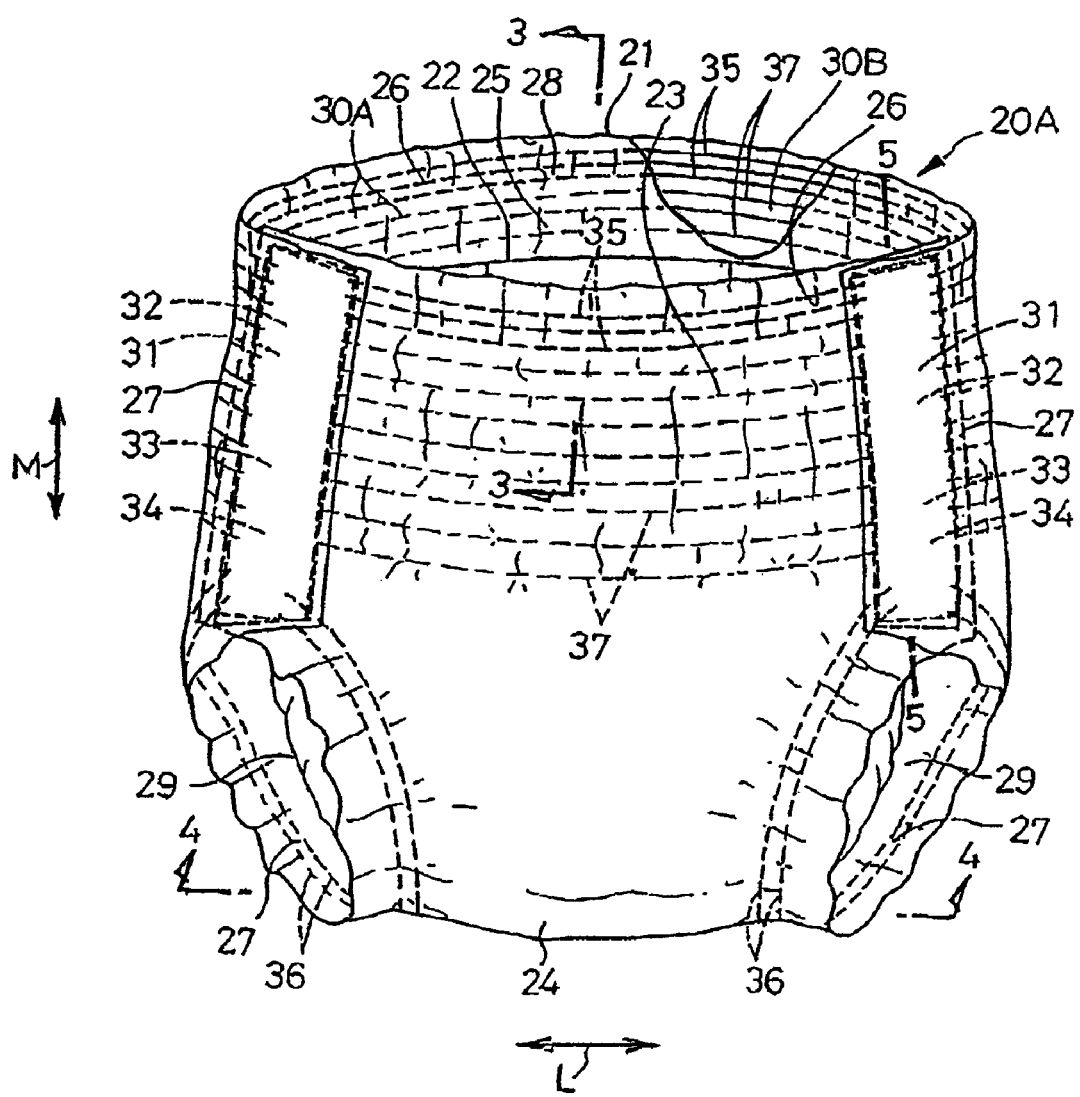
FIG. 1 is a partially cutaway perspective view showing a wearing article as a first embodiment of the invention.
Figure 2:
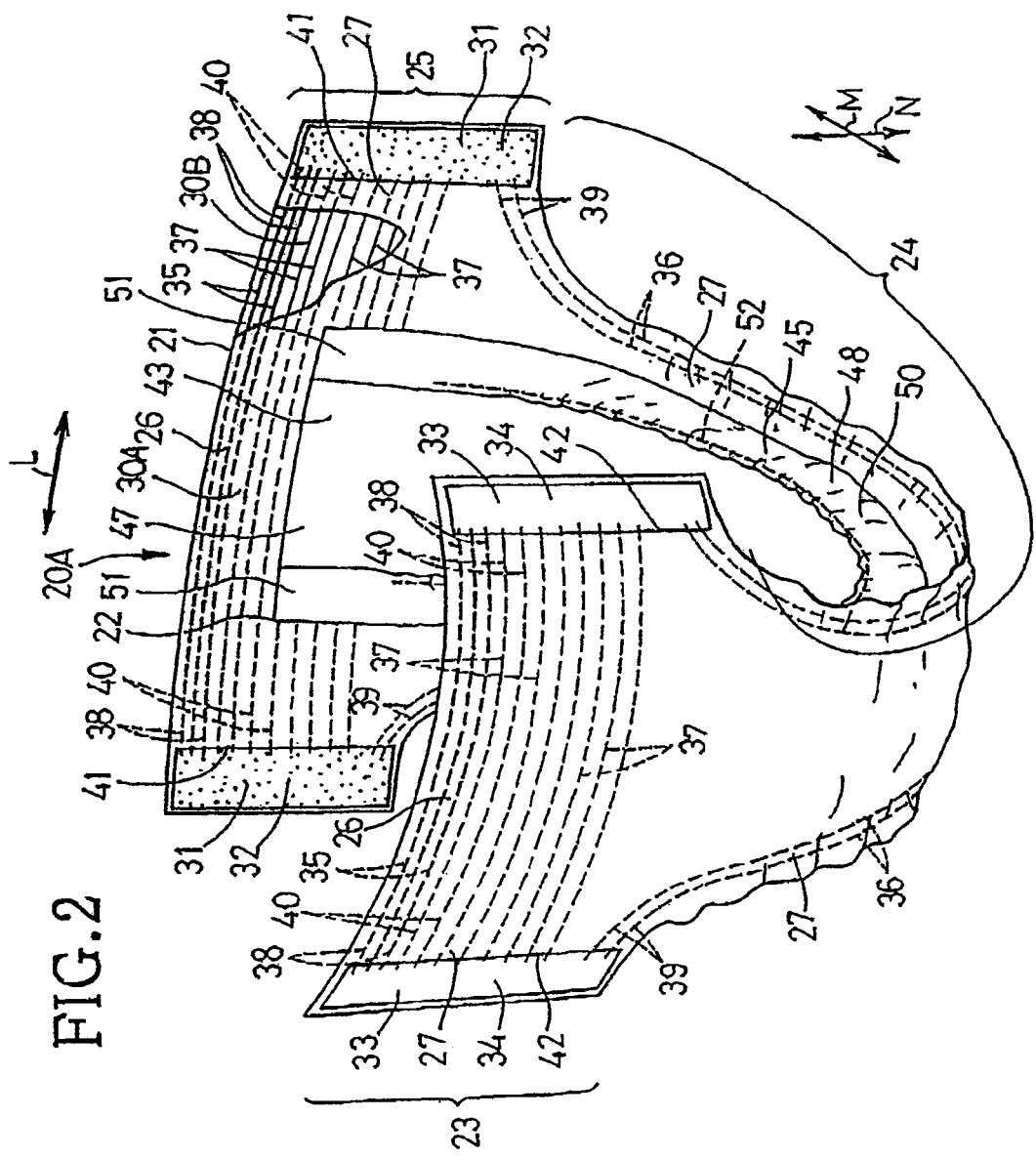
FIG. 2 is a perspective view showing this article as front and rear waist regions thereof disconnected from each other along longitudinally extending side edges of these two waist regions.
Figure 3:
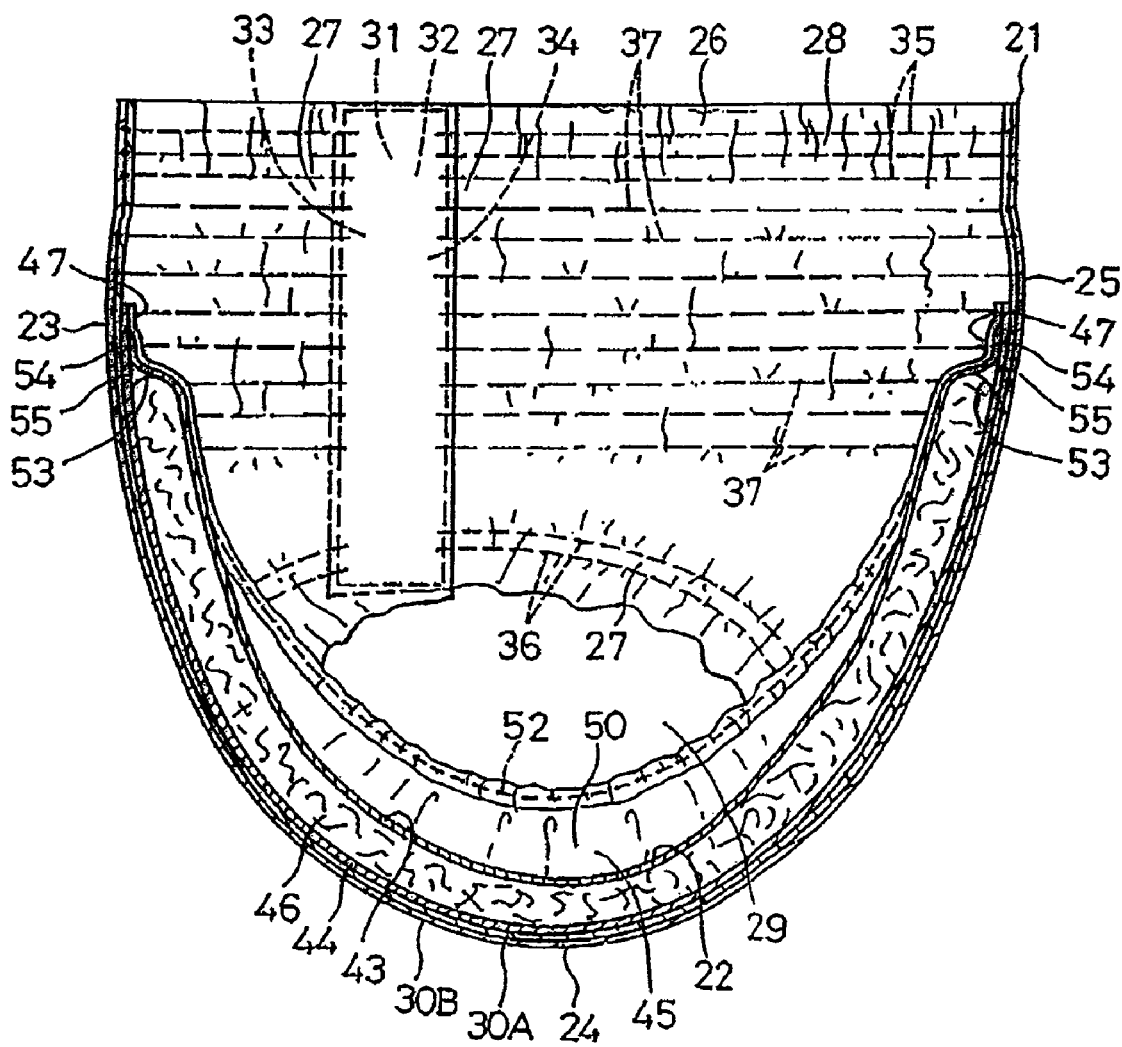
FIG. 3 is a sectional view taken along the line 3-3 in FIG. 1.
Figure 4:
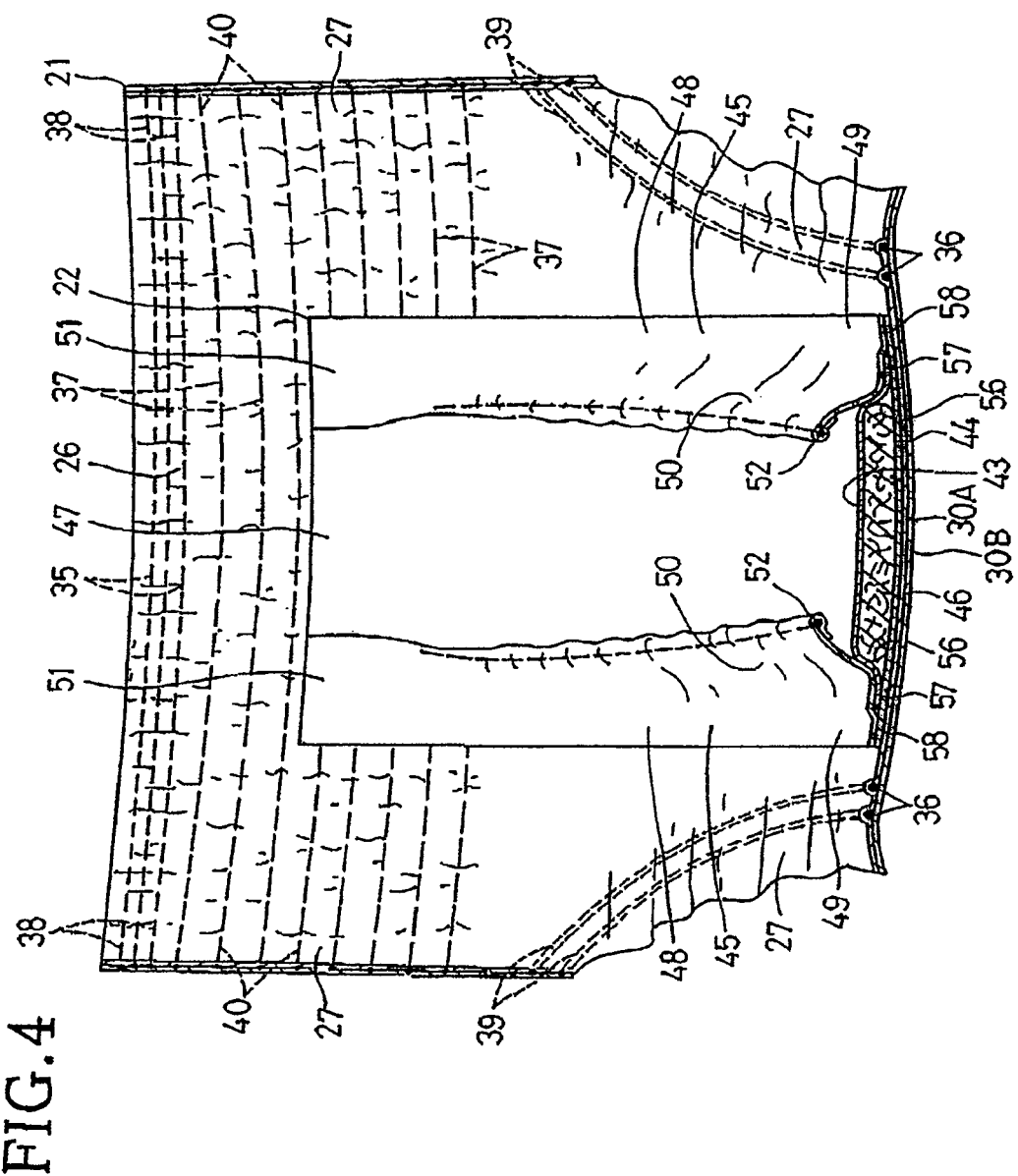
FIG. 4 is a sectional view taken along the line 4-4 in FIG. 1.
Figure 5:
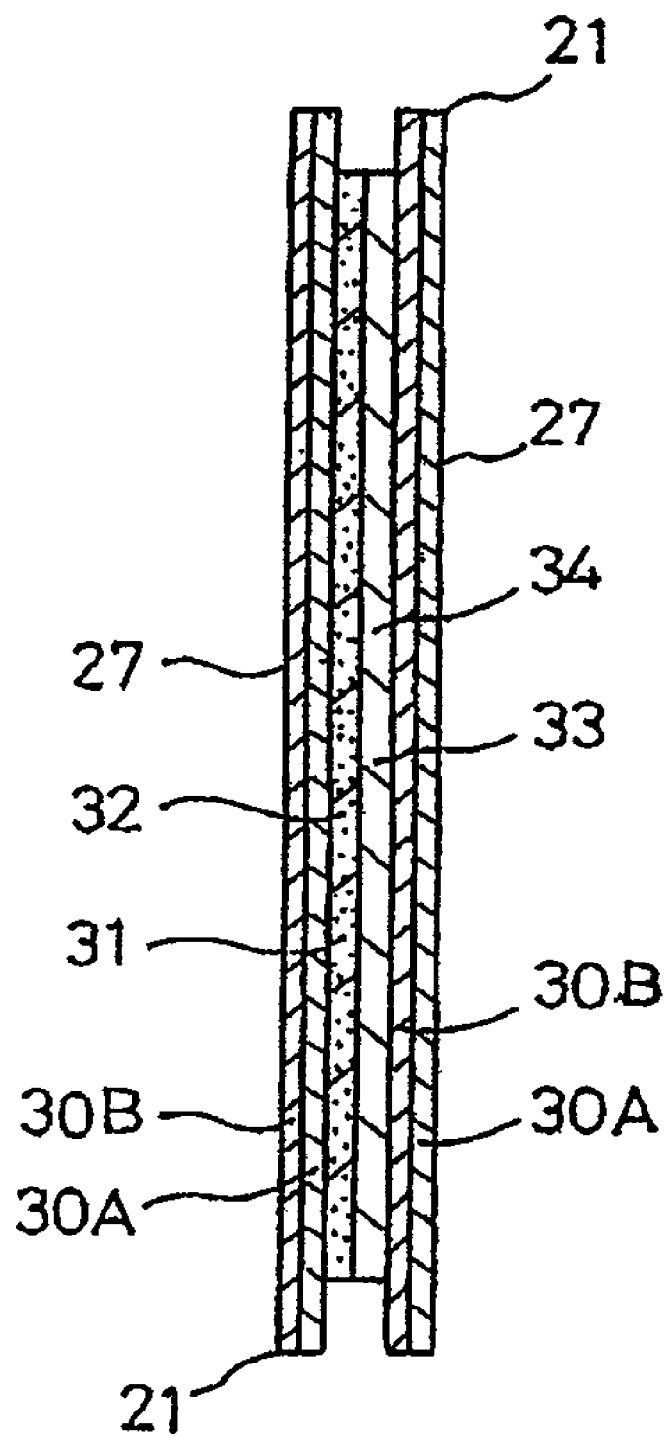
FIG. 5 is a sectional view taken along the line 5-5 in FIG. 1.

Details of a disposable wearing article according to this invention will be more fully understood from the description given hereunder with reference to the accompanying drawings.

Referring now to FIGS. 1-5, an article 20A comprises an outer sheet 21 and a liquid-absorbent inner panel 22 attached to an inner surface of the outer sheet 21. The article 20A has a front waist region 23, a rear waist region 25 opposed to the front waist region 23 and a crotch region 24 extending between these two waist regions 23, 25. The article 20A is contoured by transversely extending ends 26 in the front and rear waist regions 23, 25 and longitudinally extending side edges 27 between the front and rear waist regions 23, 25. As will be seen in FIG. 1, the article 20A is formed with a waist-hole 28 and a pair of leg-holes 29.

The outer sheet 21 is formed from sheets and has a generally hourglass-like planar shape. Specifically, the outer sheet 21 is formed from inner and outer layers 30A, 30B made of hydrophobic fibrous nonwoven fabric layers overlapped together. Mutually opposed surfaces of these inner and outer layers 30A, 30B are tightly bonded to each other without leaving any clearance left. It is possible without departing the scope of the invention to form the outer sheet 21 from three or more hydrophobic fibrous nonwoven fabric layers wherein mutually opposed surfaces of each pair of the adjacent layers are tightly bonded to each other, or to form the outer sheet 21 from two or more breathable liquid-impervious plastic film layers wherein mutually opposed surfaces of each pair of the adjacent layers are tightly bonded. It is also possible without departing from the scope of the invention to form the outer sheet 21 from a hydrophobic fibrous nonwoven fabric layer and a breathable liquid-impervious film layer wherein mutually opposed surfaces of these two layers are tightly bonded to each other.

The side edges 27 of the rear waist region 25 are provided on the respective inner surfaces with fastening zones 31 being elongate along the side edges 27 and slightly left the ends 26. Each of these fastening zones 31 is formed from an adhesive layer 32 coated with an adhesive material on the inner surface of the outer sheet 21. The side edges 27 of the front waist region 23 are provided on the respective outer surfaces with landing zones 33 operatively associated with the respective fastening zones 31. Each of these landing zones 33 is substantially the same as the fastening zone 31 in shape and size and formed from a plastic film strip 34 tightly bonded to the outer surface of the outer sheet 21. The outer layer 30B of the outer sheet 21 and the film strips 34 are tightly bonded to each other without any clearance left. The fastening zones 31 and the landing zone 31 are laid without overlapping with the inner panel 22 on the outer sheet 21. The fastening zones 31 can removably bonded to the respective landing zones 33 by means of the adhesive layer 32 wherein these fastening zones 31 can be repetitively bonded to and peeled off from the respective landing zones 33. Each of the fastening zones 31 and the landing zones 33 has a transverse dimension in a range of 10 to 40 mm and a longitudinal dimension in a range of 70 to 120 mm. Preferably, the adhesive layer 32 has a thickness dimension in a range of 5 to 100 μm. If the thickness dimension of the adhesive layer 32 is less than 5 μm, the tack strength of the adhesive material of the adhesive layer 32 also may be rapidly deteriorated. If the thickness dimension of the adhesive layer 32 exceeds 100 μm, it will be difficult to transfer the wearer's body warmth to the adhesive layer 32. In other words, the wearer's body warmth will be unable to warm the adhesive layer 32 quickly and a long time is required for the adhesive layer 32 to restore its desired tack strength. The adhesive material of the adhesive layer 32 is softened by being wormed and therefore softened by transfer of body warmth of the wearer to the adhesive layer 32 and thereby the tack strength of the adhesive layer 32 will increase.

The adhesive material of the adhesive layer 32 may be selected from conventional adhesives used in the art, for example, the group consisting of an acrylic adhesive, silicone adhesive and polyvinyl ether adhesive and, it is particularly preferable to use an acrylic adhesive of removable type, while the acrylic adhesive may be composed of polymer alone, a suitable tackiness imparting resin may added to the polymer to improve the tack strength, if desired. Acrylic polymer comprises principal monomer contributing to tackiness, comonomer contributing to cohesiveness and functional group containing monomer adapted to form crosslinked spots and these monomers and comonomer are subjected to radical polymerization or anionic polymerization. As the principal monomer, acrylic alkyl ester having Tg of −50° C. or lower is usually used. Preferred comonomer can be copolymerized with principal monomer such as acrylic ester containing lower alkyl group, methacrylic alkyl ester, vinyl acetate, styrene or acrylonitril to produce an increased in Tg. These comonomers contribute not only to improvement in the cohesiveness but also to improvement in various properties such as tackiness, water-resistance, transparency and workability. The functional group containing monomer may be used to form the crosslinked spots and, at the same time, to improve the tackiness of the adhesives. The functional group containing monomer may be selected from the group including a monomer containing carboxyl group such as acrylic acid or methacrylic acid and a monomer containing hydroxyl group, epoxy group or amino group.

The ends 26 of the outer sheet 21 are respectively provided with a plurality of waist elastic members 35 contractibly attached thereto. These waist elastic members 35 are interposed between the inner and outer layers 30A, 30B and tightly bonded to the mutually opposed surfaces of these inner and outer layers 30A, 30B while these elastic members 35 are stretched at a predetermined ratio in the transverse direction. The crotch region 23 is provided along each of its side edges 27 with a plurality of leg elastic members 36 extending along the side edges 27 and contractibly attached thereto. The leg elastic members 36 are interposed between the inner and outer layers 30A, 30B and bonded to the mutually opposed surfaces of these inner and outer layers 30A, 30B while the elastic members are stretched in their lengthwise direction at a predetermined ratio. Between the waist elastic members 35 and the leg elastic members 36 in the front and rear waist regions 23, 25, a plurality of auxiliary elastic members 37 spaced one from another in the longitudinal direction and extending in the transverse direction are contractibly attached to the article 20A. These auxiliary elastic members 37 are interposed between the inner and outer layers 30A, 30B and bonded to the mutually opposed surfaces of these inner and outer layers 30A, 30B while these elastic members 37 are stretched at a predetermined ratio in the transverse direction. The elastic members 35, 36, 37 are bonded to the inner and outer layers 30A, 30B without any clearance left between the inner and outer layers 30A, 30B and these elastic members 35, 36, 37.

Lengthwise ends 38, 39, 40 of the respective elastic members 35, 36, 37 extend to the side edges 27 of the front and rear waist regions 23, 25. In the side edges 27 of the front and rear waist regions 23, 25, the lengthwise ends 38, 39, 40 of these elastic members 35, 36, 37 are to the mutually opposed surfaces of the inner and outer layers 30A, 30B without any clearance left. The lengthwise ends 38, 39, 40 of these elastic members 35, 36, 37 terminate immediately inside mutually opposed inner side edges 41, 42 of the fastening zones 31 and the landing zones 33 without extending across these fastening zones 31 and the landing zones 33.

The inner panel 22 comprises the liquid-pervious topsheet 43 facing the wearer's skin, the liquid-impervious backsheet 44 facing away from the wearer's skin, a pair of leak-barrier cuffs 45 laid on the outer side of the topsheet 43 and the liquid-absorbent core 46 interposed between these top- and backsheets 43, 44 and bonded to respective inner surfaces of these sheets 43, 44. The panel 22 is shaped in a rectangle which is relatively long in the longitudinal direction and laid on the outer sheet 21 leaving the transversely extending ends 26 and the side edges 27 of the outer sheet 21 unoccupied and contoured by transversely extending ends 47 and longitudinally extending side edges 48. In the panel 22, the backsheet 44 is fixed to the inner surface of the outer sheet 21. The topsheet 43 is made of a hydrophilic fibrous nonwoven fabric. The backsheet 44 is made of a composite sheet composed of a breathable liquid-impervious plastic film facing the core 46 and a hydrophobic fibrous nonwoven fabric laminated with the breathable liquid-impervious plastic film and facing the outer sheet 21. The leak-barrier cuffs 45 are made of a water-repellent finished hydrophobic fibrous nonwoven fabric.

The leak-barrier cuffs 45 are laid on the side edges 48 of the panel 22 and extend between the ends 47 of the panel 22. The leak-barrier cuffs 45 respectively have proximal sections 49 fixed to the side edges 48 so as to extend in the longitudinal direction, distal sections 50 extending in parallel to the proximal 49 in the longitudinal direction and normally biased to rise up above the topsheet 43, and longitudinally opposite ends 51 collapsed inward as viewed in the transverse direction of the panel 22 and bonded in such a collapsed state to the ends 47 of the panel 22. In the vicinity of distal edges of the respective distal sections 50, elastic members 52 extending in the longitudinal direction are contractibly attached to the leak-barrier cuffs 45. In response to contraction of the elastic members 52, the distal sections 50 of the respective leak-barrier cuffs 45 contract in the longitudinal direction and rise up above the topsheet 43 to form barriers against body fluid.

The ends 47 of the panel 22 are defined by transversely extending ends 54, 55 of the top- and backsheets 43, 44, respectively, extending outward in the longitudinal direction beyond transversely extending ends 53 of the core 46 and the ends 51 of the respective leak-barrier cuffs 45. Along the ends 47, the ends 54, 55 of the top- and backsheets 43, 44, respectively, and the ends 51 of the leak-barrier cuffs 45 are overlapped together wherein the respective inner surfaces of the top- and backsheets 43, 44 are bonded to each other and the topsheet 43 is bonded to the inner surfaces of the respective leak-barrier cuffs 45. The side edges 48 of the panel 22 are defined by side edges 57, 58 of the top- and backsheets 43, 44, respectively, extending outward in the transverse direction beyond side edges 56 of the core 46 and the proximal sections 49 of the respective leak-barrier cuffs 45. In the vicinity of the side edges 48, the side edges 57 of the topsheet 43 extends outward in the transverse direction slightly beyond the side edges 56 of the core 46 and the side edges 58 of the backsheet 44 as well as the proximal sections 49 of the leak-barrier cuffs 45 extend in the transverse direction further beyond the side edges 57. Along the side edges 48, the side edges 57, 58 of the top- and backsheets 43, 44, respectively, and the proximal sections 49 of the respective leak-barrier cuffs 45 are overlapped together wherein the respective inner surfaces of the top- and backsheets 43, 44 are bonded together and the inner and outer surfaces of the top- and backsheets 43, 44, respectively, are bonded to the inner surfaces of the respective leak-barrier cuffs 45.

Bonding of the inner layer 30A to the outer layer 30B, bonding of the outer layer 31B to the film strip 34, bonding of the elastic members 35, 36, 37 to the inner and outer layers 30A, 30B, bonding of the outer sheet 21 to the backsheet 44, bonding of the topsheet 43 to the backsheet 44, bonding of the leak-barrier cuffs 45 to the top- and backsheets 43, 44 and bonding of the elastic members 52 to the leak-barrier cuffs 45 are carried out using adhesive materials (not shown). The adhesive materials are applied on the inner and outer layers 30A, 30B and the sheets 21, 43, 44 and the cuffs 45 preferably in a pattern selected from the group of a spiral pattern, wavy pattern, zigzag pattern, dotted pattern and striped pattern. The adhesive layers may be selected from the group consisting of a hot melt adhesive, acrylic adhesive and rubber adhesive.

To put the article 20A on the wearer's body, the fastening zones 31 are bonded to the associated landing zones 33 to connect the front and rear waist regions 23, 25 along the side edges 27 of thereof. Body fluid discharged on the article 20A put on the wearer's body in this manner is absorbed by the core 46 through the topsheet 43 and contained therein. The side edges 27 of the front waist region 23 are defined by a pair of the inner and outer layers 30A, 30B overlapped together, of which the mutually opposed surfaces are tightly bonded to each other with no clearance left therebetween, and thereby body warmth of the wearer is reliably transferred from the wearer to the adhesive layer 32 through the side edges 27 of the front waist region 23. Consequentially, the adhesive layer 32 deteriorated due to setting the adhesive material thereof is softened and restores its desired tack strength as the time elapses.

A peel strength at room temperature between the fastening zones 31 and the landing zones 33 bonded to each other is in a range of 3 to 8 N/25 mm (preferably in a range of 4 to 6 N/25 mm), the peel strength on one hour after the fastening zones 31 have been bonded to the associated landing zones 33 at a temperature of 36 to 40° C. is in a range of 5 to 11 N/25 mm (preferably in a range of 6 to 9 N/25 mm) and the peel strength three hours after the fastening zones 31 have been bonded to the associated landing zones 33 at a temperature of 36 to 40° C. is in a range of 6 to 12 N/25 mm (preferably in a range of 7 to 10 N/25 mm).

When a temperature near body warmth of the wearer, i.e., a temperature of about 36° C. to about 40° C., transfers the side edges 27 of the front waist region 23, the tack strength of the adhesive layers 31's adhesive material increases. Consequently, the peel strength between the fastening zones 31 and the associated landing zones 33 also increases. The peel strength between the fastening zones 31 and the associated landing zones 33 was measured in such a way as will be described below.

(1) The side edges 27 of the front waist region 23 including the landing zones 33 and the side edges 27 of the rear waist region 25 including the fastening zones 31 were cut from the article 20A to prepare first through third samples for measurement of peel strength (dimension of each sample: 100 mm×40 mm; and dimension of each fastening zone 31 and each landing zone 33: 80 mm×25 mm). For measurement of the peel strength, a Measuring instrument "AUTO-GRAPH AG-I" manufactured by Shimadzu Corporation in Japan was used. Of a curve plotted for the peel strength versus the peel dimension when the samples are peeled off from each other in the longitudinal direction, the peel strength of the plotted curve portion showing nearly even strength was adapted as that of each of the samples.

(2) A roller weighing 700 g was pressed against the first through third samples to bond the fastening zones 31 to the landing zones 33. The samples having the respective fastening zones 31 bonded to the landing zones 33 were left at constant temperature and humidity for 30 minutes. For each of the samples, one end of the sample (the end of the front waist region 23) and the other end of the sample (the end of the rear waist region 25) were held by chucks (chuck interval: 10 mm) and the fastening zone 31 was peeled (by T-peel) off from the landing zone 33 at 300 mm/min and thereafter the roller weighing 700 was pressed against the samples to bond the fastening zone 31 again to the landing zone 33.

(3) Immediately after the fastening zone 31 had been bonded again to the landing zone 33, the one end and the other end of the first sample were held by the chucks (chuck interval: 10 mm) and the fastening zone 31 was peeled (by T-peel) off from the landing zone 33 at 300 mm/min. The peel strength in this course was measured by the above-mentioned instrument. The peel strength of the first sample measured in this manner was in a range of 3 to 8 N/25 mm.

(4) The second sample having the fastening zone 31 bonded to the landing zone 33 was left within an oven at a temperature of 40° C. for 1 hour. After 1 hour had elapsed, the one end and the other end of the second sample were held by the chucks (chuck interval: 10 mm) and the fastening zone 31 was peeled (by T-peel) off from the landing zone 33 at 300 mm/min. The peel strength in this course was measured by the above-mentioned instrument. The peel strength of the second sample measured in this manner was in a range of 5 to 11 N/25 mm.

(5) The third sample having the fastening zone 31 bonded to the landing zone 33 was left within an oven at a temperature of 40° C. for 3 hours. After 3 hours had elapsed, the one end and the other end of the third sample were held by the chucks (chuck interval: 10 mm) and the fastening zone 31 was peeled (by T-peel) off from the landing zone 33 at 300 mm/min. The peel strength in this course was measured by the above-mentioned instrument. The peel strength of the third sample measured in this manner was in a range of 6 to 12 N/25 mm.

Even if the ends 38, 39, 40 of the elastic members 35, 36, 37 extending toward the side edges 27 of the front waist region 23 are interposed between the inner and outer layers 30A, 30B, the end 38, 39, 40 of the respective elastic members 35, 36, 37 terminate in the vicinity of the inner side edges 42 of the respective landing zones 33 and additionally, the respective elastic embers 35, 36, 37 are tightly bonded to the mutually opposed surfaces of these inner and outer layers 30A, 30B with no clearance left between the mutually opposed surfaces of the inner and outer layers 30A, 30B as well as between these inner and outer layers 30A, 30B and the ends 38, 39, 40 of the respective elastic members 35, 36, 37. This means that body warmth of the wearer can be reliably transferred to the adhesive layer 32 through the side edges 27 of the front waist region 23.

Figure 6:
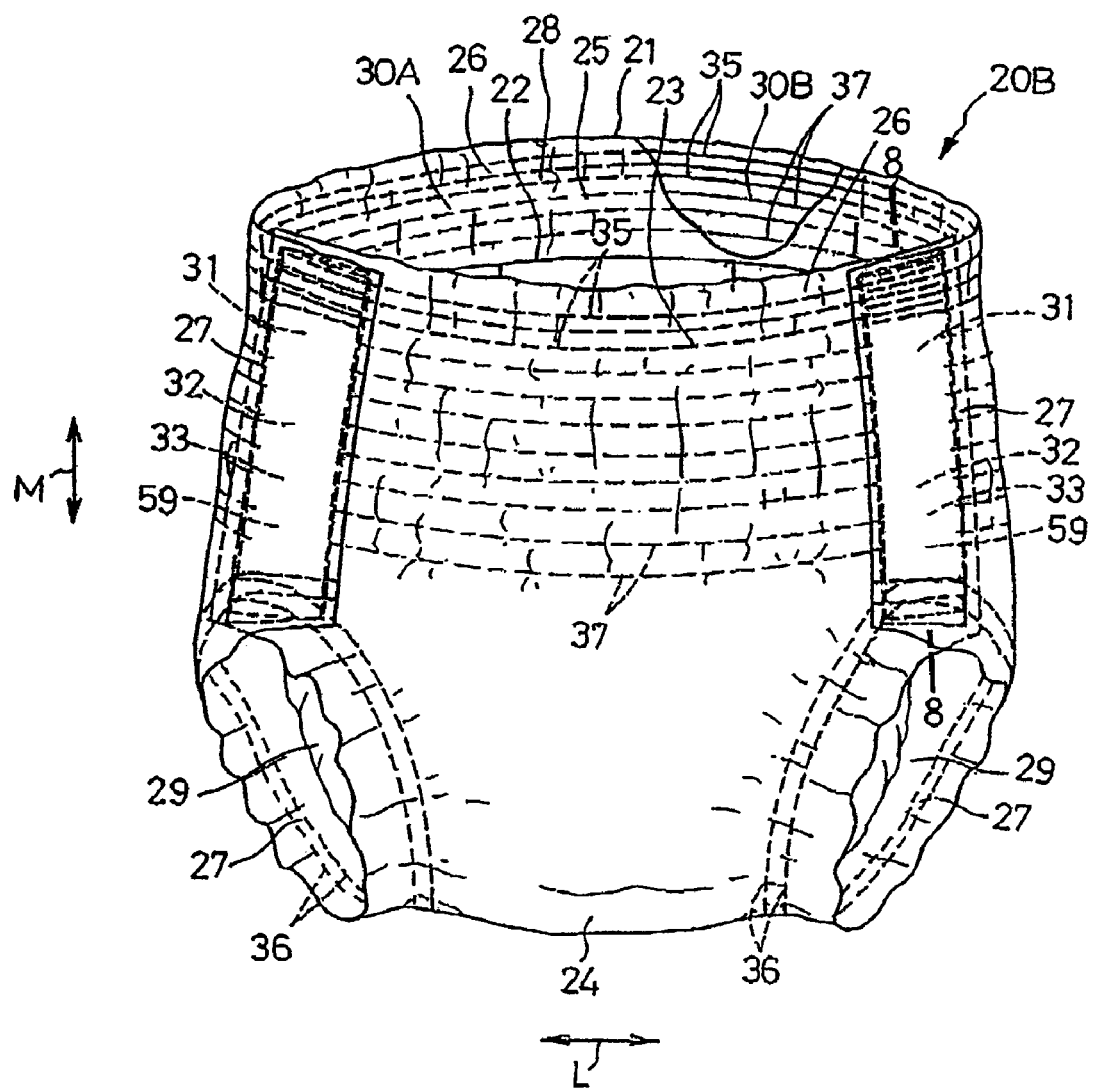
FIG. 6 is a partially cutaway perspective view showing a wearing article as a second embodiment of the invention.
Figure 7:
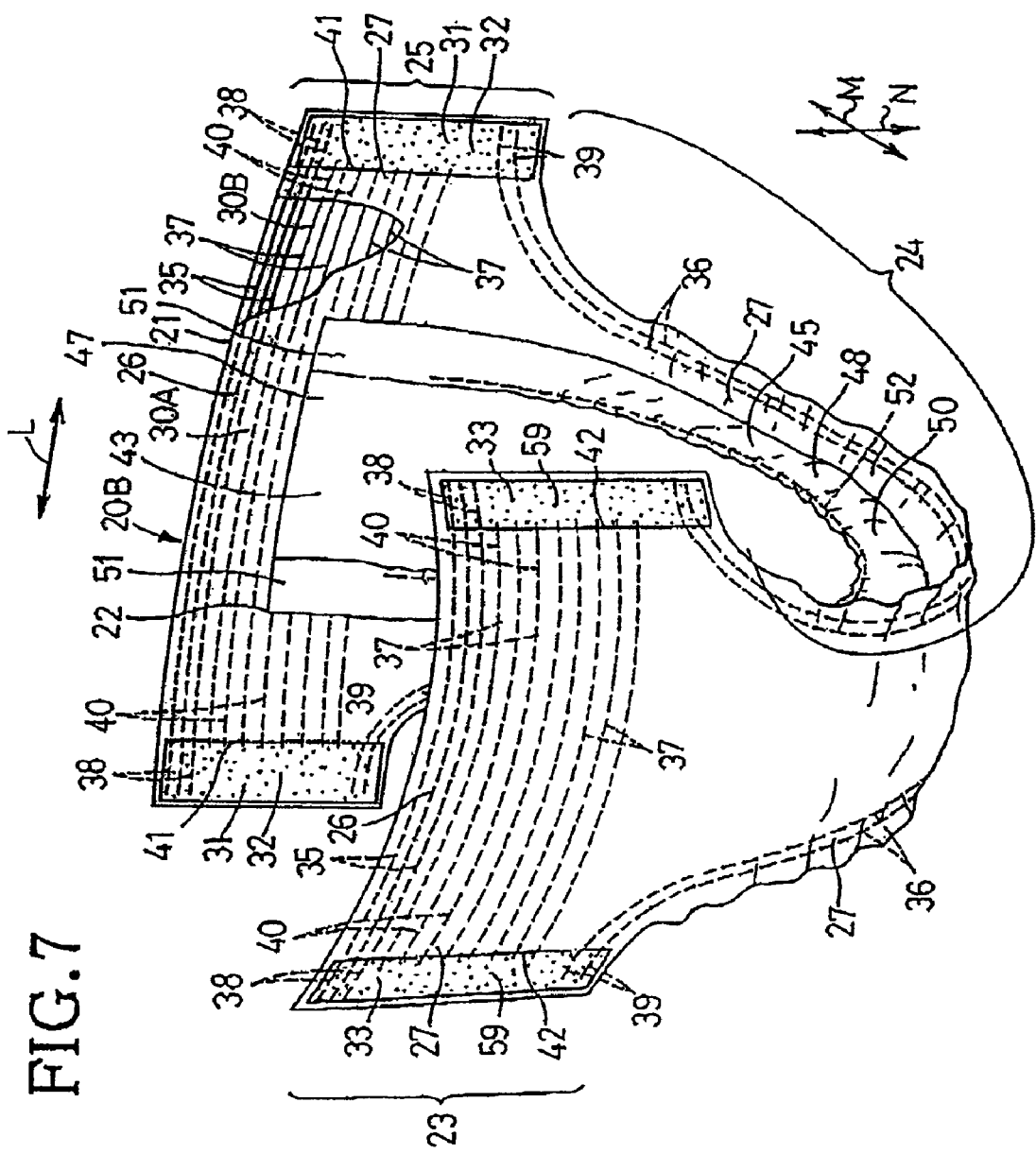
FIG. 7 is a perspective view showing this article as front and rear waist regions thereof disconnected from each other along longitudinally extending side edges of these two waist regions.
Figure 8:
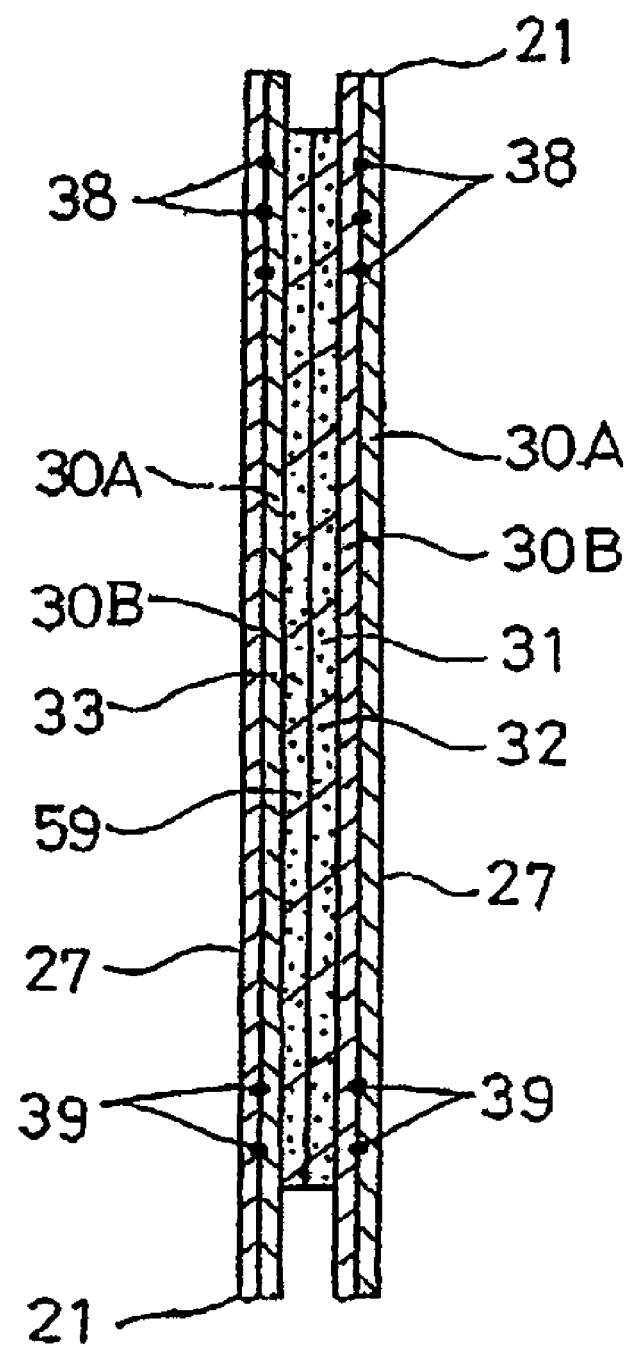
FIG. 8 is sectional view taken along the line 8-8 in FIG. 6.
Figure 9:
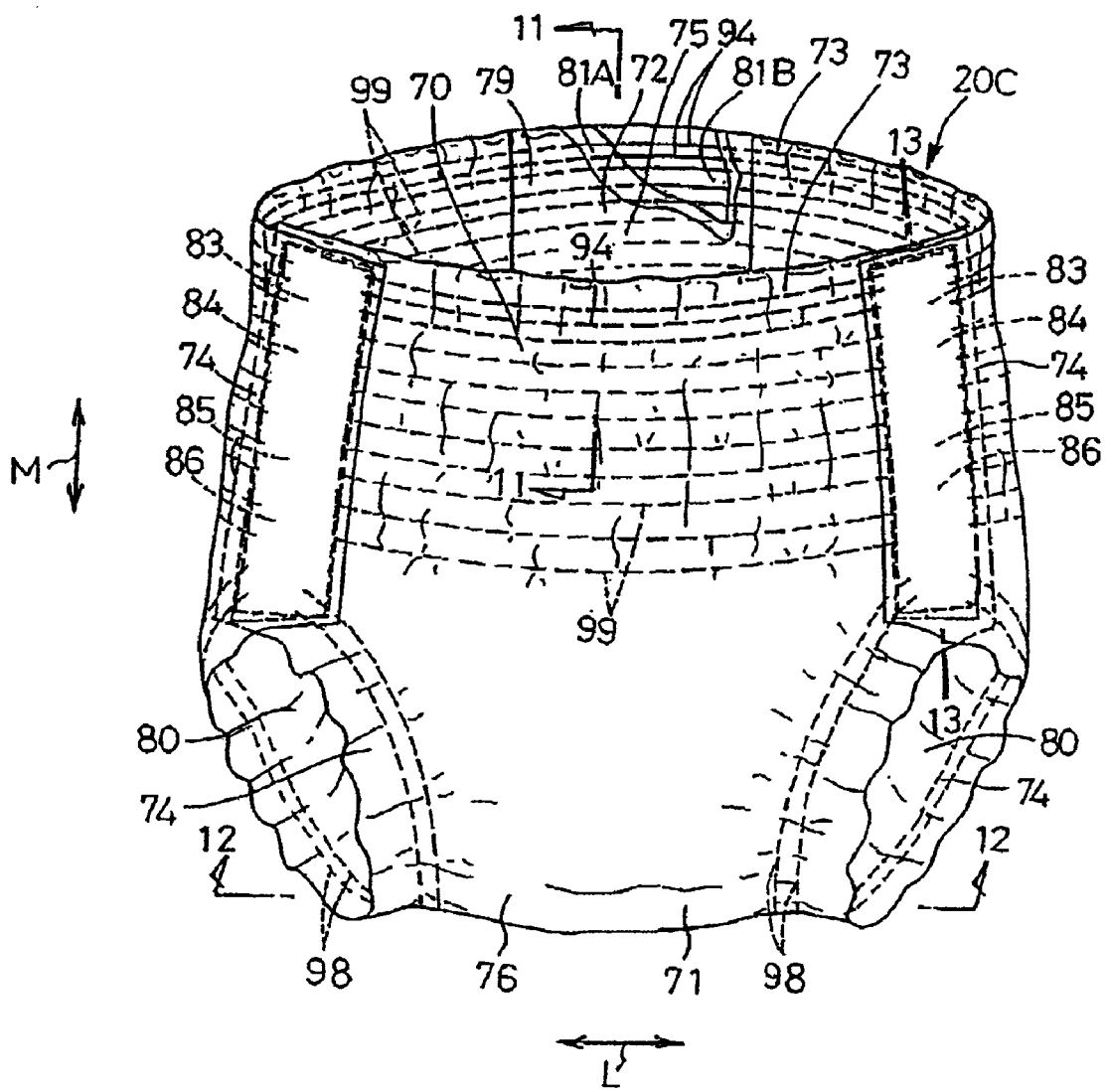
FIG. 9 is a partially cutaway perspective view showing a wearing article as a third embodiment of the invention.
Figure 10:
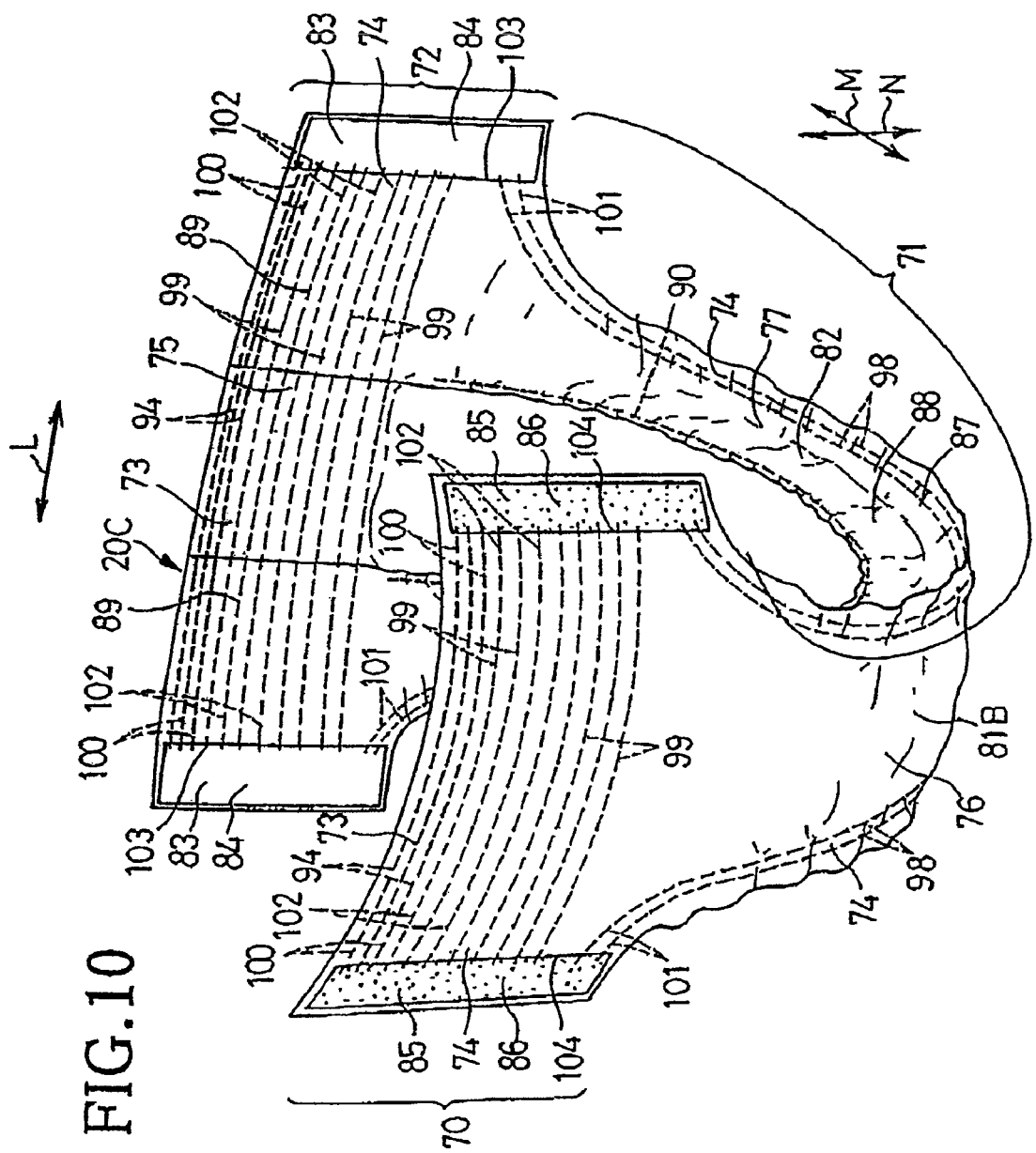
FIG. 10 is a perspective view showing this article as front and rear waist regions disconnected from each other along longitudinally extending side edges of these two waist regions.
Figure 11:
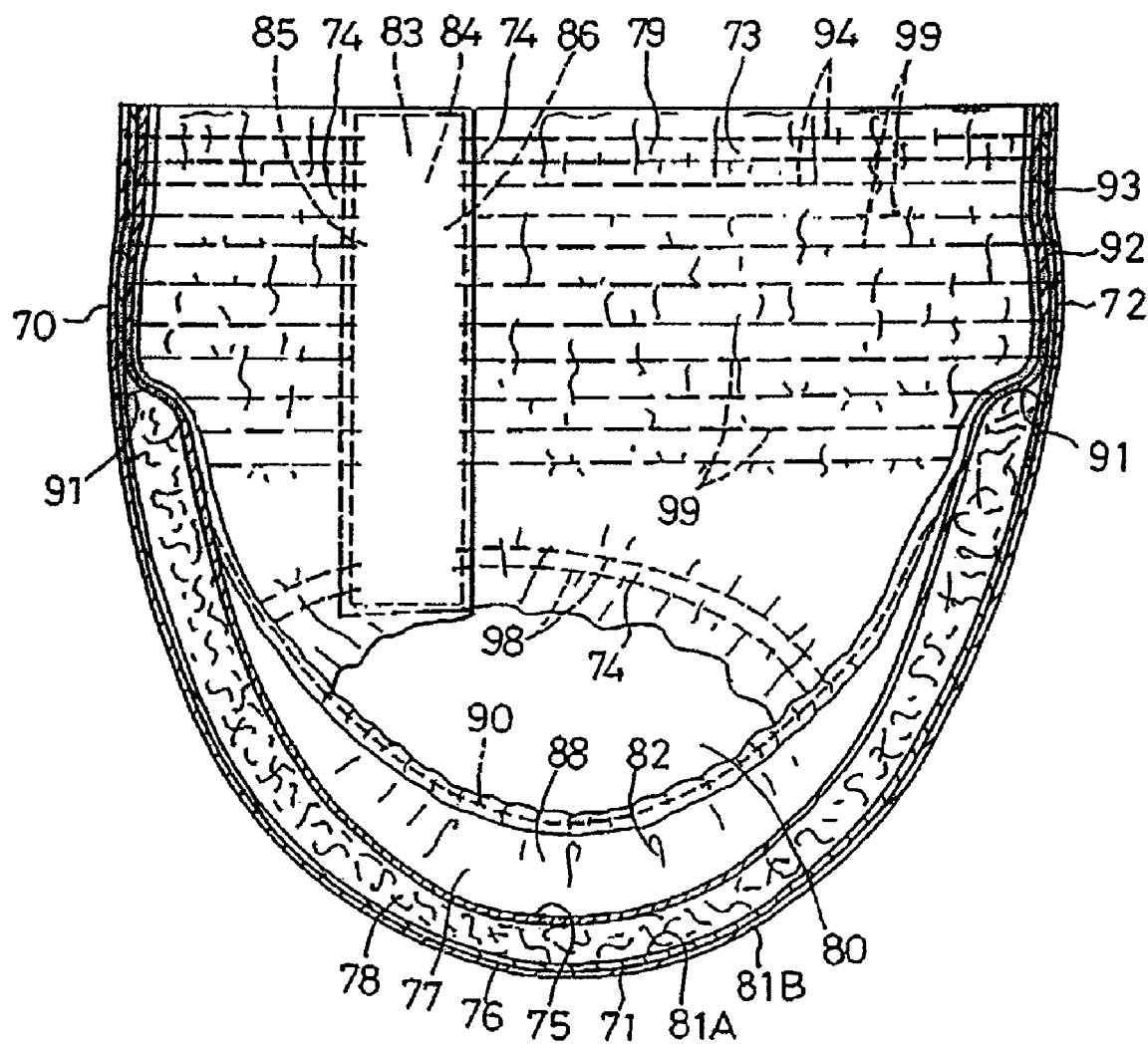
FIG. 11 is a sectional view taken along the line 11-11 in FIG. 9.
Figure 12:
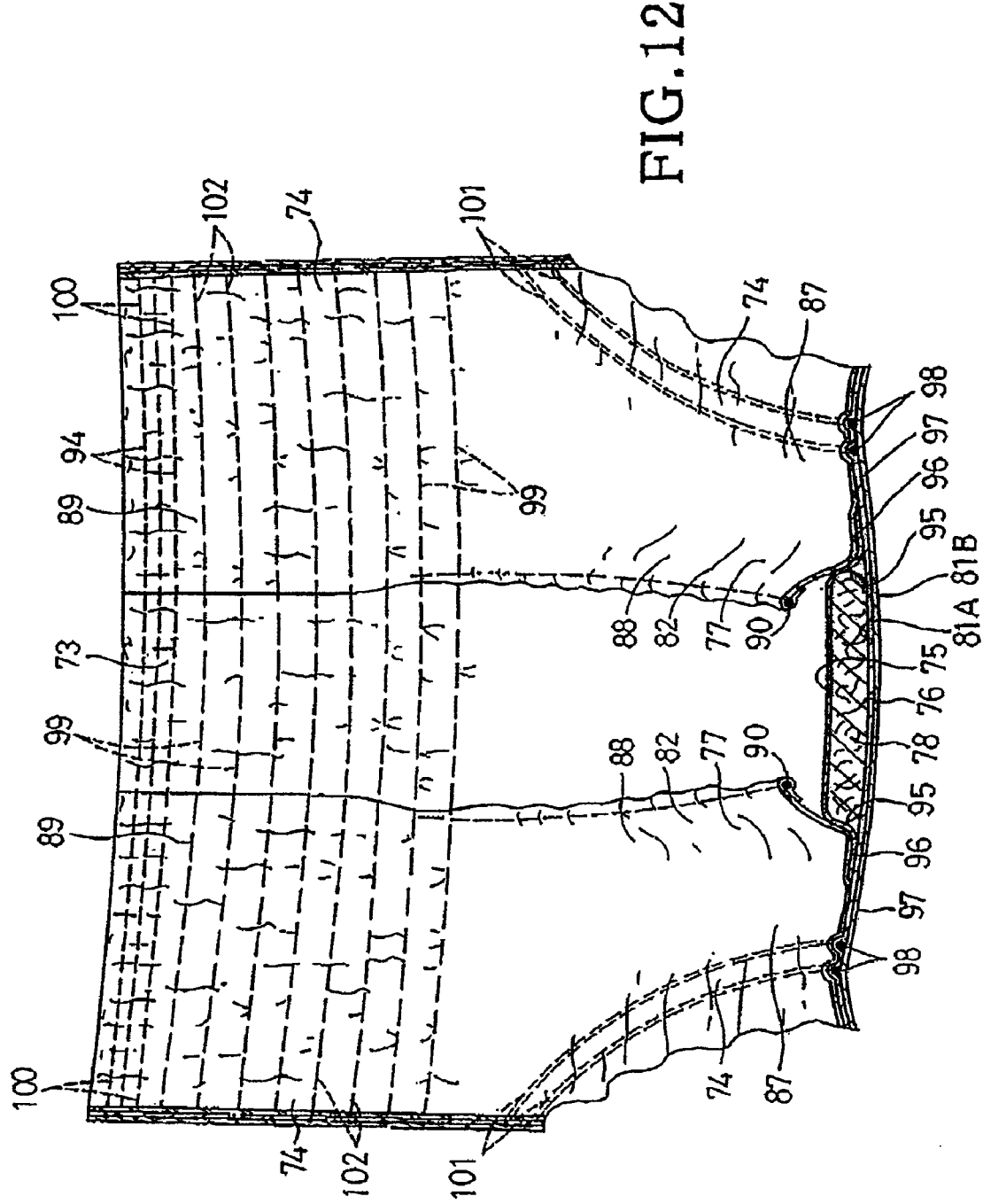
FIG. 12 is a sectional view taken along the line 12-12 in FIG. 9.
Figure 13:
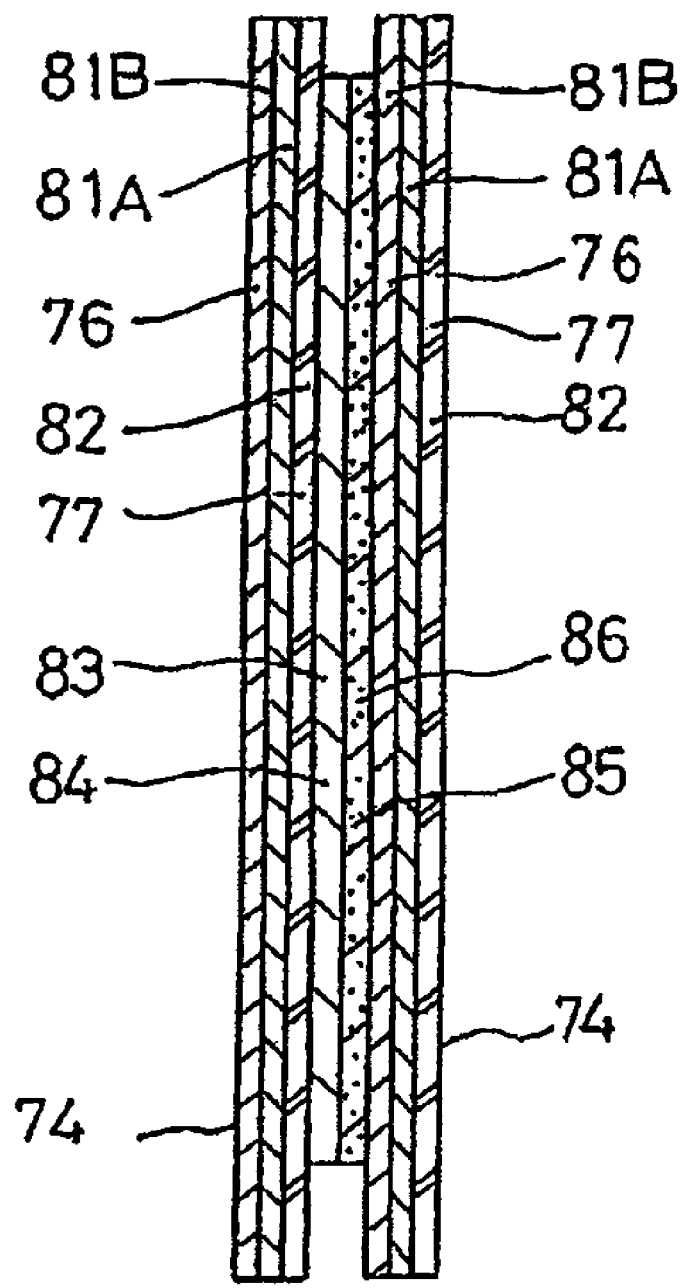
FIG. 13 is a sectional view taken along the line 13-13 in FIG. 9.
Figure 14:
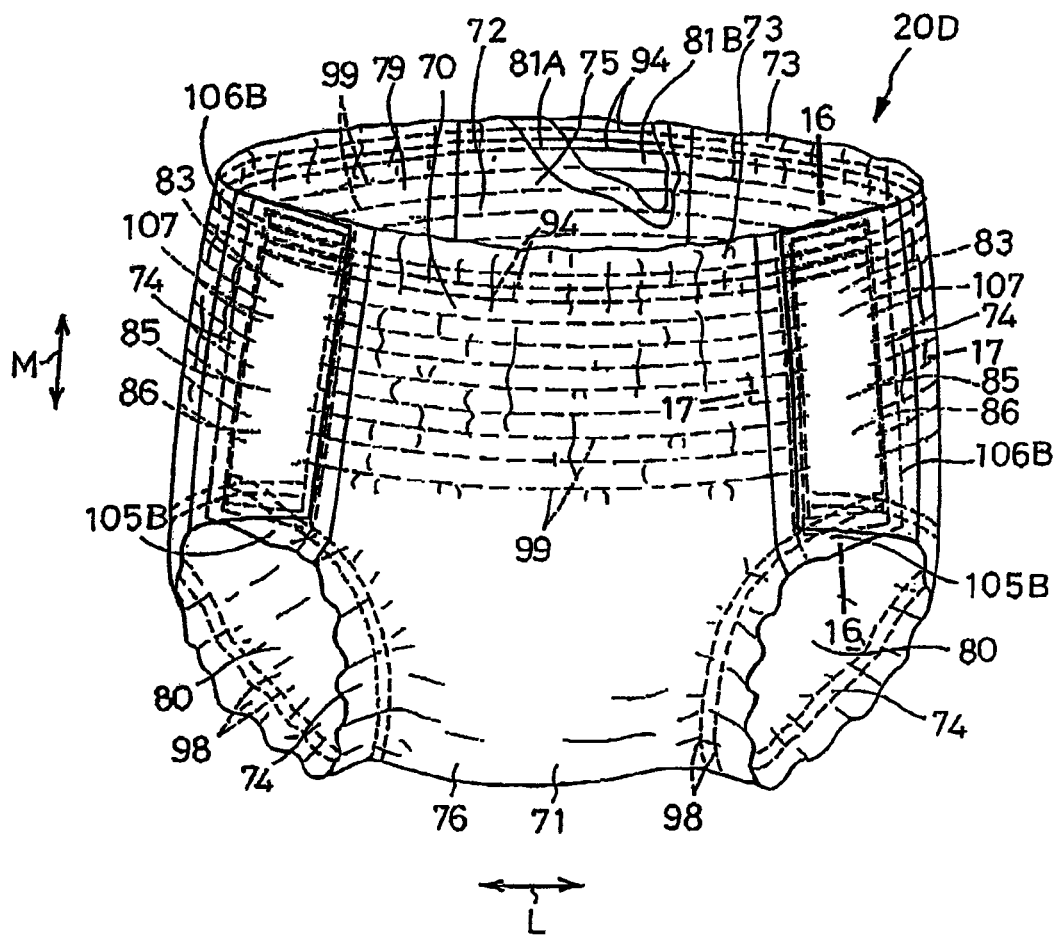
FIG. 14 is a partially cutaway perspective view showing a wearing article as a fourth embodiment of the invention.
Figure 15:
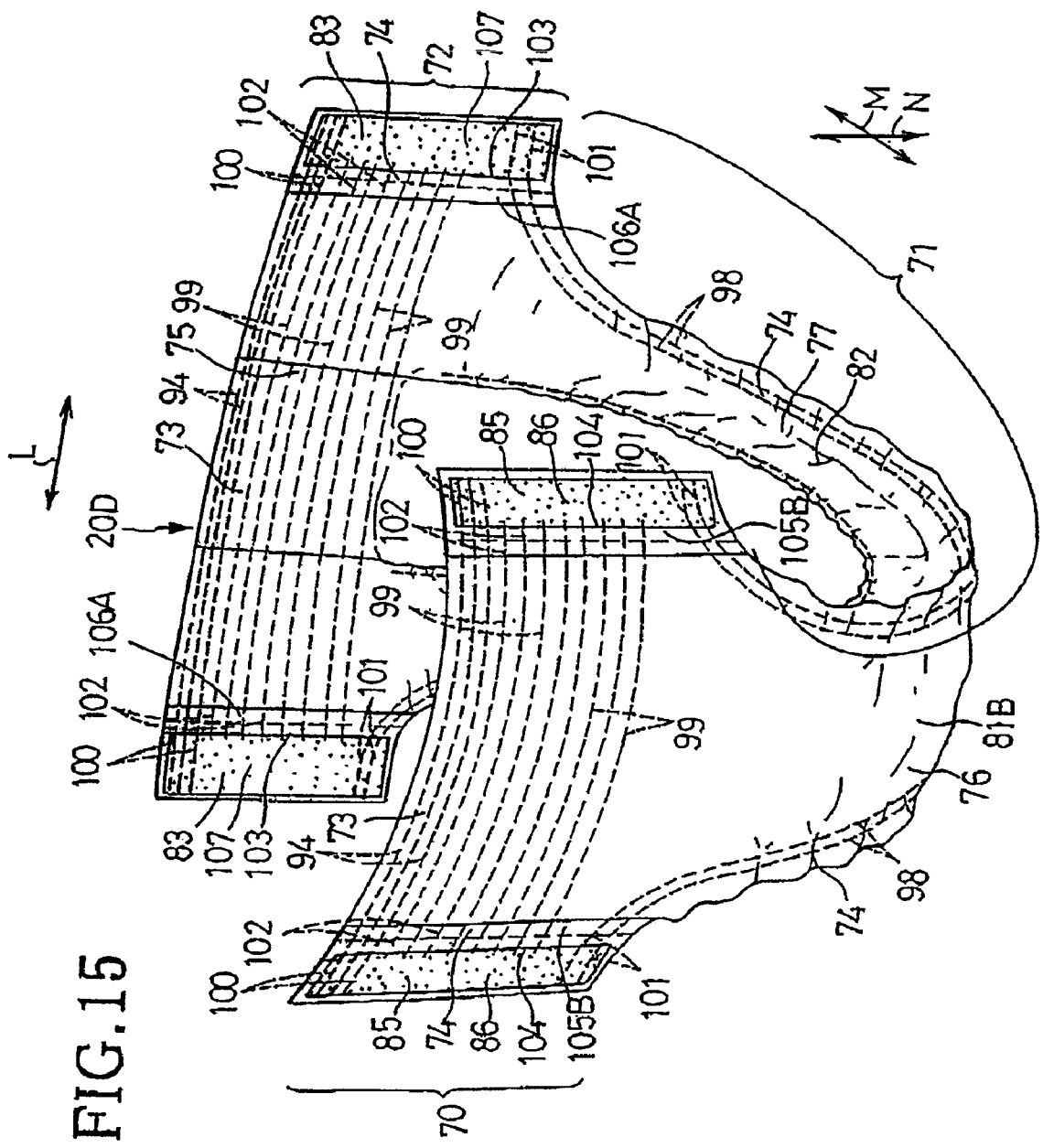
FIG. 15 is a perspective view showing this article as front and rear waist regions disconnected from each other along longitudinally extending side edges of these two waist regions.
Figure 16:
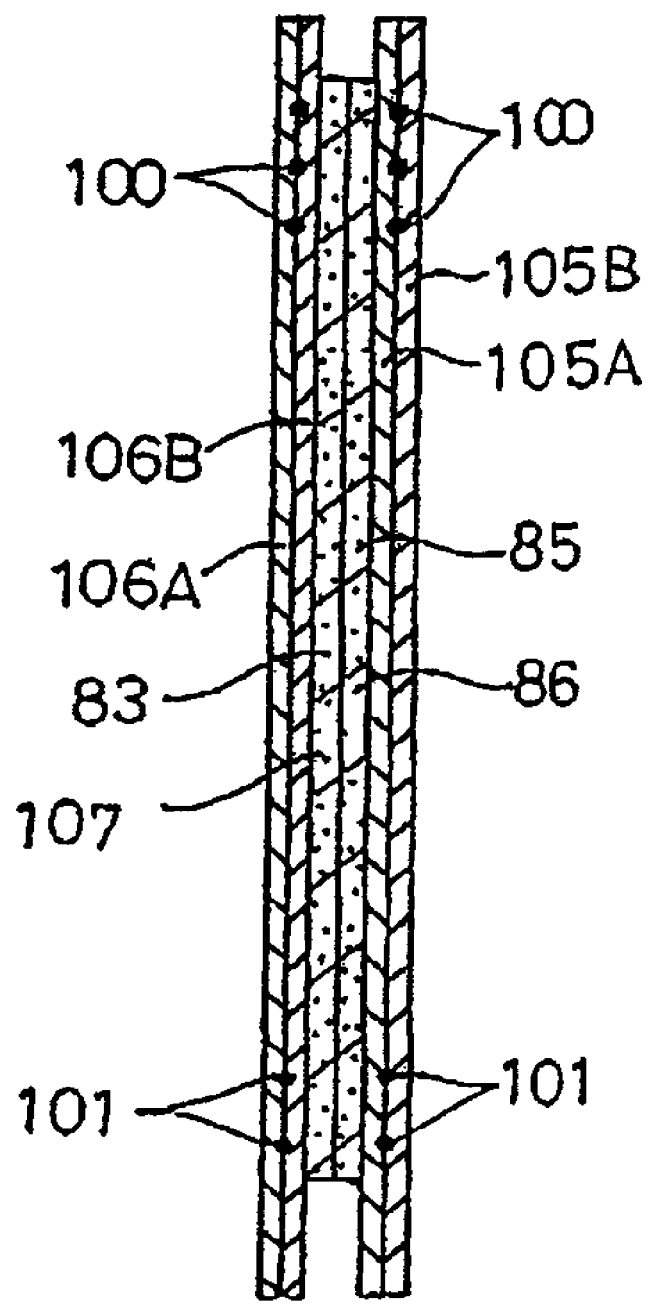
FIG. 16 is a sectional view taken along the line 16-16 in FIG. 14.
Figure 17:
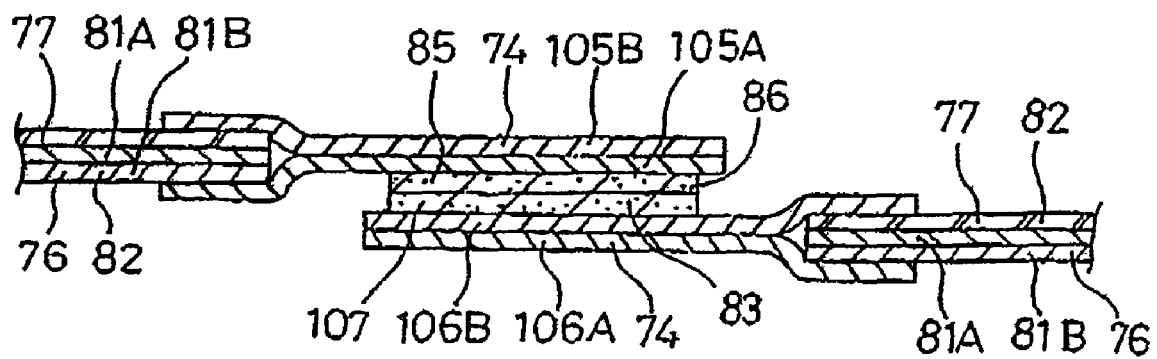
FIG. 17 is a sectional view taken along the line 17-17 in FIG. 14.

Referring to FIG. 6 through 8 showing a second embodiment of the invention, an article 20B is similar to the article 20A of the first embodiment of the invention except that the landing zones 33 are formed from an adhesive layer 59 and ends 38, 39 of elastic members 35, 36, respectively, extend across the fastening zones 31 and the landing zones 33. The remaining arrangements in this article 20B are denoted by the same reference numerals as those in the article 20A and not redundantly described.

The fastening zones 31 are formed from the adhesive layer 32 applied with an adhesive material on the side edges 27 of the rear waist region 25. The landing zones 33 are formed from an adhesive layer 59 applied with an adhesive material on the side edges 27 of the front waist region 23. The same adhesive materials may be used for the adhesive layer 32 and the layer of adhesive 59. Preferably, the adhesive layer 59 has a thickness dimension in a range of 5 to 100 µm similar to the adhesive layer 32. It is preferable, however, that well-known self-adhesive material is used for the adhesive layers 32, 59.

Of the elastic members 35, 36, 37 interposed between the inner and outer layers 30A, 30B, while the ends 40 of the elastic members 37 extend across neither the fastening zones 31 nor the landing zones 33 and terminate in the vicinity of the mutually opposed inner side edges 41, 42 of these zones 31, 33, the ends 38 of the elastic members 35 as well as the ends 39 of the elastic members 36 extend across both the fastening zones 31 and the landing zones 33.

Even if the elastic members 35, 36 interposed between the inner and outer layers 30A, 30B extend across the fastening zones 31 and the landing zones 33, the inner and outer layers 30A, 30B and the elastic members 35, 36, 37 are tightly bonded to the mutually opposed surfaces of the inner and outer layers 30A, 30B so that no clearance is left between the mutually opposed surfaces of the inner and outer layers 30A, 30B as well as between the inner and outer layers 30A, 30B and the ends 38, 39, 40 of the respective elastic members 35, 36, 37. This means that body warmth of the wearer can be reliably transferred to the adhesive materials of the adhesive layers 32, 59 through the side edges 27 of the front waist region 23.

Referring to FIG. 9 through 13, an article 20C has a front waist region 70, a rear waist region 72 opposed to the front waist region 70 and a crotch region 71 extending between these waist regions 70, 72 and is contoured by transversely extending ends 73 in the front and rear waist regions 70, 72, respectively, and longitudinally extending side edges 74 between the front and rear waist regions 70, 72. The article 20C comprises a liquid-pervious topsheet 75 facing the wearer's skin, a liquid-impervious backsheet 76 facing away from the wearer's skin, a pair of leak-barrier cuffs 77 laid on the outer side of the topsheet 75 and a liquid-absorbent core 78 interposed between the top- and backsheets 75, 76 and bonded to respective inner surfaces of these sheets 75, 76. The side edges 74 in the crotch region 71 describe circular arcs which are convex inward as viewed in the transverse direction of the article 20C. Thus the article 20C has a generally hourglass-like planar shape. The article 20C is formed with a waist-hole 79 and a pair of leg-holes 80 as will be seen in FIG. 9.

The topsheet 75 is formed from a hydrophilic fibrous nonwoven fabric layer. The backsheet 76 is formed from a pair of inner and outer layers 81A, 81B made of hydrophobic fibrous nonwoven fabric layers overlapped together. It is possible without departing from the scope of the invention to form the backsheet 76 from a breathable liquid-impervious plastic film layer and a hydrophobic fibrous nonwoven fabric layer having mutually opposed surfaces tightly bonded to each other. The leak-barrier cuffs 77 are formed from a water-repellent finished hydrophobic fibrous nonwoven fabric layer 82.

The side edges 74 of the rear waist region 72 are formed on the respective inner surfaces with fastening zones 83 being elongate along the side edges 74 and slightly left the ends 73. Each of these fastening zones 83 is formed from a plastic film strip 84 tightly bonded to the barrier cuffs 77 in a zone not overlapped with the core 78. The side edges 74 of the front waist region 70 are formed on the respective outer surfaces with landing zones 85 operatively associated with the respective fastening zones 83, the landing zones 85 being elongate along the side edges 74 and slightly left the ends 73. Each of these landing zones 85 is formed from an adhesive layer 86 applied with an adhesive material on the outer layer 81B in a zone not overlapped with the core 78. The fastening zones 83 can removably bonded to the respective landing zones 85 and can be repetitively bonded to and peeled off from the respective landing zones 85. The fastening zones 83 and the landing zones 85 are identical one to another in shape as well as in size. Specifically, each of them has a transverse dimension in a range of 10 to 40 mm and a longitudinal dimension in a range of 70 to 120 mm. Similarly to the adhesive material of the adhesive layer 32 in the article 20A in the first embodiment of the invention, the adhesive material may be selected from the group including an acrylic self-adhesive, silicone self-adhesive, polyvinyl ether self-adhesive and rubber self-adhesive. Preferably, the adhesive layer 86 has a thickness dimension in a range of 5 to 100 µm similarly to the adhesive layer 32 in the first embodiment.

The leak-barrier cuffs 77 are laid on the side edges 74 and extend between the ends 73 in the longitudinal direction. The leak-barrier cuffs 77 respectively have proximal 87 fixed to the side edges 74 so as to extend in the longitudinal direction, distal sections 88 extending in parallel to the proximal sections 87 in the longitudinal direction and normally biased to rise up above the topsheet 75, and longitudinally opposite ends 89 collapsed inward as viewed in the transverse direction of the article 20C and bonded in such a collapsed state to the ends 73 of the article 20C. In the vicinity of distal edges of the respective distal sections 88, elastic members 90 extending in the longitudinal direction are bonded to the leak-barrier cuffs 77 while the elastic members 90 are stretched in the longitudinal direction at a predetermined ratio. In response to contraction of the elastic members 90, the distal sections 88 of the respective leak-barrier cuffs 77 contract in the longitudinal direction and rise up above the topsheet 75 to form barriers against body fluid.

The ends 73 are defined by longitudinally opposite ends 92, 93 of the top- and backsheets 75, 76, respectively, extending outward in the longitudinal direction beyond longitudinally opposite ends 91 of the core 78 and the ends 89 of the respective leak-barrier cuffs 77. Along the ends 73, the ends 92, 93 of the top- and backsheets 75, 76, respectively, and the ends 89 of the leak-barrier cuffs 77 are overlapped together wherein the respective inner surfaces of the top- and backsheets 75, 76 are bonded to each other and the outer surface of the topsheet 75 is bonded to the inner surfaces of the respective leak-barrier cuffs 77.

The side edges 74 are defined by transversely opposite side edges 96, 97 of the top- and backsheets 75, 76, respectively, extending outward in the transverse direction beyond transversely opposite side edges 95 of the core 78 and the proximal sections 87 of the respective leak-barrier cuffs 77. In the vicinity of the side edges 74, the side edges 96 of the topsheet 75 extends outward in the transverse direction slightly beyond the side edges 95 of the core 78 and the side edges 97 of the backsheet 76 as well as the proximal sections 87 of the leak-barrier cuffs 77 extend in the transverse direction slightly beyond the side edges 96. Along the side edges 74, the side edges 96, 97 of the top- and backsheets 75, 76, respectively, and the proximal sections 87 of the respective leak-barrier cuffs 77 are tightly overlapped together wherein the respective inner surfaces of the top- and backsheets 75, 76 are tightly bonded together and the inner and outer surfaces of the top- and backsheets 75, 76, respectively, are tightly bonded to the inner surfaces of the respective leak-barrier cuffs 77.

The side edges 74 of the front and rear waist regions 70, 72 are substantially defined by the side edges 97 of the backsheet 76 and the proximal sections 87 of the respective leak-barrier cuffs 77. Along the side edges 74 of the front and rear waist regions 70, 72, the inner and outer layers 81A, 81B and the leak-barrier cuff 77 are tightly bonded together and the mutually opposed surfaces of these inner and outer layers 81A, 81 and the leak-barrier cuff 77 are tightly bonded one to another with no clearance left among them.

The ends 73 are respectively provided with a plurality of waist elastic members 94 extending in the transverse direction contractibly attached thereto. The waist elastic members 94 are interposed between the inner and outer layers 81A, 81B and tightly bonded to the mutually opposed surfaces of these inner and outer layers 81A, 81B while these elastic members 94 are stretched at a predetermined ratio in the transverse direction. Each of the side edges 74 is provided with a plurality of leg elastic members 98 extending in the longitudinal direction and contractibly attached thereto. The leg elastic members 98 are interposed between the inner and outer layers 81A, 81B and tightly bonded to the mutually opposed surfaces of these inner and outer layers 81A, 81B while the elastic members 98 are stretched in the longitudinal direction at a predetermined ratio. Between the waist elastic members 94 and the leg elastic members 98 in the front and rear waist regions 70, 72, a plurality of auxiliary elastic members 99 spaced one from another in the longitudinal direction and extending in the transverse direction are contractibly attached to the article 20C. These auxiliary elastic members 99 are interposed between the inner and outer layers 81A, 81B and tightly bonded to the mutually opposed surfaces of these inner and outer layers 81A, 81B while these elastic members 99 are stretched at a predetermined ratio in the transverse direction. The elastic members 94, 98, 99 are tightly bonded to the inner and outer layers 81A, 81B with no clearance left between the inner and outer layers 81A, 81B and these elastic members 94, 98, 99.

The ends 100, 101, 102 of these elastic members 94, 98, 99 extend toward the side edges 74 of the front and rear waist regions 70, 72. On the side edges 74 of the front and rear waist regions 70, 72, respectively, the ends 100, 101, 102 of the respective elastic members 94, 98, 99 are tightly bonded to the mutually opposed surfaces of the inner and outer layers 81A, 81B with no clearance left between the inner and outer layers 81A, 81B and these elastic members 94, 98, 99, i.e., these elastic members 94, 98, 99 are held in close contact with the inner and outer layers 81A, 81B. The ends 100, 101, 102 of these elastic members 94, 98, 99 extend across neither the fastening zones 83 nor the landing zones 85 but terminate at mutually opposed inner side edges 103, 104 of these zones 83, 85.

Bonding of the topsheet 75 and the backsheet 76 to each other, bonding of the top- and backsheets 75, 76 to the leak-barrier cuffs 77, bonding of the elastic members 90 to the leak-barrier cuffs 77, bonding of the inner and outer layers 81A, 81B to each other, bonding of the leak-barrier cuffs 77 to the film strip 84, bonding of the elastic members 94, 98, 99 to the inner and outer layers 81A, 81B are carried out using adhesive materials (not shown). The adhesive materials are applied on the inner and outer layers 81A, 81B and the sheets 75, 76 and the cuffs 77 preferably in a pattern selected from the group of a spiral pattern, wavy pattern, zigzag pattern, dotted pattern and striped pattern. The adhesives may be selected from the group consisting of a hot melt adhesive, acrylic adhesive and rubber adhesive.

To put the article 20C on the wearer's body, the fastening zones 83 are bonded to the associated landing zones 85 to connect the front and rear waist regions 70, 72 along the side edges 74 thereof. Body fluid discharged on the article 20C put on the wearer's body in this manner is absorbed by the core 78 through the topsheet 75 and contained therein. The side edges 74 of the front waist region 70 are defined by three inner and outer layers 81A, 81B and the leak-barrier cuffs 77 overlapped together, of which the mutually opposed surfaces are tightly bonded one to another with no clearance left among the mutually opposed surfaces. Consequently, body warmth of the wearer is reliably transferred from the wearer of the article 20C to the adhesive layer 86 through the side edges 74 of the front waist region 70 and thereby the adhesive layer 86 can be prevented from deteriorating a tack strength of the adhesive material by restoring the tack strength deteriorated due to setting of the adhesive material.

A peel strength at room temperature between the fastening zones 83 and the landing zones 85 bonded one to another is in a range of 3 to 8 N/25 mm (preferably in a range of 4 to 6 N/25 mm). The peel strength one hour after the fastening zones 83 have been bonded to the associated landing zone 85 at a temperature of 36 to 40° C. is in a range of 5 to 11 N/25 mm (preferably in a range of 6 to 9 N/25 mm) and the peel strength three hours after the fastening zones 83 have been bonded to the associated landing zones 85 at a temperature of 36 to 40° C. is in a range of 6 to 12 N/25 mm (preferably in a range of 7 to 10 N/25 mm). The peel strength between the fastening zones 83 and the landing zones 85 was measured in the same way as in the case of the article 20A in the first embodiment of the invention. When a temperature near body warm of the wearer, i.e., a temperature of about 36 to about 40° C., transfers the side edges 74 of the front waist region 70, the tack strength of the adhesive material increases. Consequently, the peel strength between fastening zones 83 and the landing zones 85 also increases.

Referring to FIGS. 14-17 showing a fourth embodiment of the invention, an article 20D is similar to the article 20C in the third embodiment of the invention except that major part of transversely opposite side edges 74 of front and rear waist regions 70, 72 are formed from a pair of inner and outer layers 105A, 105B, 106A, 106B made of fibrous nonwoven fabric layers, respectively, fastening zones 83 are formed from an adhesive layer 107 and longitudinally opposite ends 100, 101 of elastic members 94, 98, respectively, extend across the fastening zones 83 and the landing zones 85. The remaining arrangements in this article 20D are denoted by the same reference numerals as those in the article 20C and not redundantly described.

The side edges 74 of the front waist region 70 are substantially defined by a pair of the inner and outer layers 105A, 105B separately of the top- and backsheets 75, 76 and the leak-barrier cuffs 77. The mutually opposed surfaces of these inner and outer layers 105A, 105B are tightly bonded together with no clearance left therebetween. The inner layer 105A facing the wearer's skin is hydrophilic and has a water absorbing capacity higher than that of the outer layer 105B facing away from the wearer's skin. The outer layer 105B may be either hydrophilic or hydrophobic. There are two method available to make a water absorbing capacity of the inner layer 105A higher than that of the outer layer 105B. According to the first method, the inner layer 105A is added with an adequate amount of hydrophilically modifying agent by coating the surface of fibers constituting the inner layer 105A with the hydrophilically modifying agent or incorporating the hydrophilically modifying agent into the fibers constituting the inner layer 105A. According to the second method, a fiber density of the inner layer 105A is adjusted to be higher than that of the outer layer 105B and a basis weight of the inner layer 105A is adjusted to be higher than that of the outer layer 105B. It is also possible to use the first method in combination with the second method. The side edges 74 of the rear waist region 72 substantially defined by a pair of inner and outer layers 106A, 106B made of hydrophilic or hydrophobic inner and outer layers separately of the top- and backsheets 75, 76 and the leak-barrier cuffs 77. The mutually opposed surfaces of the inner and outer layers 106A, 106B are tightly bonded together with no clearance left therebetween. The inner and outer layers 106A, 106B may be hydrophilic or hydrophobic.

Along the side edges 74 in the front and rear waist regions 70, 72, the side edges 96, 97 of the top- and backsheets 75, 76, respectively, and the proximal sections 87 of the leak-barrier cuffs 77 extend outward in the transverse direction slightly beyond the side edges 95 of the core 78 and the layers 105A, 105B, 106A, 106B extend outward in the transverse direction beyond the proximal sections 87 of the cuffs 77 and the side edges 96, 97 of the sheets 75, 76. Along the side edges 74 in the front and rear waist regions 70, 72, the side edges 96, 97 of the top- and backsheets 75, 76 and the proximal sections 87 of the leak-barrier cuffs 77 are interposed between the layers 105A, 105B and between the layers 106A, 106B, respectively and inner and outer surfaces of the sheets 75, 75 and the cuffs 77 are bonded to respective mutually opposed surfaces of the layers 105A, 105B, 106A, 106B. The side edges 74 in the crotch region 71 are defined by the side edges 96, 97 of the top- and backsheets 75, 76 extending outward in the transverse direction beyond the side edges 95 of the core 78 and the distal sections 87 of the respective leak-barrier cuffs 77. Along the side edges 74 in the crotch region 71, the side edges 96, 97 of the top- and backsheets 75, 76 and the proximal sections 87 of the leak-barrier cuffs 77 are overlapped together and inner and outer surfaces of these sheets 75, 76 and the cuffs 77 are bonded together.

Each of the fastening zones 83 is formed from adhesive layers 107 applied with adhesive materials on the inner surface of the rear waist region 72 along the side edge 74. The adhesive layers 107 are provided on a region not overlapped with the core 78. Each of the landing zones 85 is also formed from an adhesive layer 86 applied with adhesive materials on the outer surface of the front waist region 70 along the side edges 74. The adhesive layers 86 are provided on a region not overlapped with the core 78. For an adhesive material of the adhesive layer 107, the same adhesive material as that for the adhesive layer 86 is for used the adhesive layer 107 and has a thickness dimension in a range of 5 to 100 μm.

These waist elastic members 94 are interposed between the layers 81A, 81B, 105A, 105B, 106A, 106B and tightly bonded to the mutually opposed surfaces of these layers 81A, 81B, 105A, 105B, 106A, 106B while these elastic members 94 are stretched at a predetermined ratio in the transverse direction. The leg elastic members 98 are interposed between the layers 81A, 81B, 105A, 105B, 106A, 106B and tightly bonded to the mutually opposed surfaces of these layers 81A, 81B, 105A, 105B, 106A, 106B while the elastic members 98 are stretched in the longitudinal direction at a predetermined ratio. The auxiliary elastic members 99 are interposed between the layers 81A, 81B, 105A, 105B, 106A, 106B and tightly bonded to the mutually opposed surfaces of these layers 81A, 81B, 105A, 105B, 106A, 106B while these elastic members 99 are stretched at a predetermined ratio in the transverse direction. The elastic members 94, 98, 99 are tightly bonded to the layers 81A, 81B, 105A, 105B, 106A, 106B with no clearance left between the layers 81A, 81B, 105A, 105B, 106A, 106B and these elastic members 94, 98, 99.

Ends 100, 101, 102 of the respective elastic members 94, 98, 99 extend toward the side edges 74 of the front and rear waist regions 70, 72. Along the side edges 74 of the front waist region 70, the ends 100, 101, 102 of these elastic members 94, 98, 99 are tightly bonded to the mutually opposed surfaces of the layers 105A, 105B, 106A, 106B with no clearance left between the layers 105A, 105B, 106A, 106B and these elastic members 94, 98, 99. The ends 102 of the auxiliary elastic members 99 extend across neither the fastening zones 83 nor the landing zones 85 but terminate is the vicinity of mutually opposed inner side edges 103, 104 of these zones 83, 85. The ends 100 of the waist elastic members 94 and the ends 101 of the leg elastic members 98 extend across both the fastening zones 83 and the landing zones 85. The ends 102 of the auxiliary elastic members 99 extend across neither the fastening zones 83 nor the landing zones 85 but terminate in the vicinity of mutually opposed inner side edges 103, 104 of these zones 83, 85. While the elastic members 94, 98 extend across both the fastening zones 83 and the landing zones 85, no clearance is left between the mutually opposed surfaces of the layers 105A, 105B, between the mutually opposed surfaces of the layers 106A, 106B and between the layers 105A, 105B, 106A, 106B and the ends 100, 101, 102 of the elastic members 94, 98, 99, so that these mutually opposed layers and, these elastic members and the layers sandwiching the elastic members are tightly bonded one to another. Consequently, body warmth of the wearer is reliably transferred from the wearer to the side edges 74 of the front waist region 70.

In the side edges 74 of the front waist region 70, since a water absorbing capacity of the inner layer 105A defining a surface of the article facing the wearer's skin is higher than that of the outer layer 105B defining a surface of the article facing away the wearer's skin, there is unlikely that body fluid of the wearer such as sweat absorbed by the inner layer 105A might be transferred from the outer layer 105B to the outer layer 105B and vaporized on the outer layer 105B. In this way, since the body fluid absorbed in the inner layer 105A is prevented from vaporizing on the outer layer 105B, the temperature of the adhesive material of the adhesive layer is prevented from dropping due to the vaporization heat.

Stock materials for the fibrous nonwoven fabric layers may be selected from the group consisting of spun lace-, needle punch-, melt blown-, thermal bond-, spun bond- and chemical bond-nonwoven fabric layers. Component fibers of these nonwoven fabric layers may be selected from the group consisting of polyester-, polyacrylonitril-, polyvinyl chloride-, polyethylene-, polypropylene- and polystyrene-based fibers. It is also possible without departing from the scope of the invention to use the component fibers selected from the group consisting of core-sheath conjugate fibers, side-by-side conjugate fibers, modified macaroni fibers, microporous fibers and fused type conjugate fibers. The film used here is a stretched plastic film obtained by extrusion-molding a thermoplastic synthetic resin into the film which is then subjected to monoaxial or biaxial stretching.

The core 46, 78 comprises a mixture of particulate or fibrous super-absorbent polymer and fluff pulp or particulate or fibrous super-absorbent polymer and fluff pulp and thermoplastic synthetic resin fiber, in any case, compressed to a desired thickness. The core 46, 78 is in its entirety wrapped with water-pervious sheet (not shown) such as tissue paper or hydrophilic fibrous nonwoven fabric in order to prevent the core 46, 78 from getting out of its shape.

In the article 20A in the first embodiment of the invention, the landing zones 33 may be formed from the adhesive layer 59 as in the article 20B in the second embodiment of the invention instead of the film strip 34. In the article 20B, the landing zones 33 may be formed from the film strip 34 as in the article 20A instead of the adhesive layer 59. In the article 20C in the third embodiment of the invention, the fastening zones 83 may be formed from the adhesive layer 107 as in the article 20D in the fourth embodiment of the invention instead of the filmstrip 84. In the article 20D, the fastening zone 83 may be formed from the film strip 84 as in the article 20C instead of the adhesive layer 107. While the front waist region 23, 70 in the illustrated articles 20A, 20B, 20C, 20D corresponds to the first waist region as defined in Claims and the rear waist region 25, 72 in the illustrated articles 20A, 20B, 20C, 20D corresponds to the second waist region as defined by Claims, the front waist region 23, 70 may correspond to the second waist region as defined by Claims and the rear waist region 25, 72 may correspond to the first waist region as defined in Claims.

What is claimed is:

1. A disposable wearing article, comprising:
a first waist region;
a second waist region;
a crotch region extending in a longitudinal direction of said article between said first and second waist regions;
transversely extending ends of said first and second waist regions;
longitudinally extending side edges between said transversely extending ends;
an absorbent core extending in the longitudinal direction from the crotch region into the first and second waist regions;
fastening zones provided on innermost surfaces of said longitudinally extending side edges of said first waist region, said innermost surfaces being adapted to face, in use, a wearer's body;
landing zones provided on outermost surfaces of said longitudinally extending side edges of said second waist region so that said fastening zones are directly releasably fastenable to said landing zones, said outermost surfaces being adapted to face, in use, away from the wearer's body;
said longitudinally extending side edges of said second waist region comprising plural sheets having mutually opposed surfaces tightly bonded to each other;
one of (a) said fastening zones and (b) said landing zones comprising a first adhesive layer applied on said innermost surface of the respective longitudinally extending side edge of said first waist region;
the other of (a) said fastening zones and (b) said landing zones comprising at least one of (i) a plastic film strip tightly bonded to said innermost surface of the respective longitudinally extending side edge of said first waist region and (ii) a second adhesive layer applied on the outermost surface of the respective longitudinally extending side edge of said second waist region,
said second adhesive layer being adapted to be softened, in use, by the wearer's body warmth transferred through the tightly bonded sheets of the respective longitudinally extending side edge of said second waist region;
wherein said landing zones are positioned without overlapping the absorbent core to facilitate heat transfer, in use, from the wearer's body to the second adhesive layers,
wherein
a peel strength between said fastening zones and said landing zones in a state being directly, releasably bonded to each other at room temperature is in a range of 3 to 8 N/25 mm,
said peel strength one hour after said fastening zones have been directly, releasably bonded to said landing zones is in a range of 5 to 11 N/25 mm at a temperature of 36 to 40° C., and
said peel strength three hours after said fastening zones have been directly, releasably bonded to said landing zones is in a range of 6 to 12 N/25 mm at a temperature of 36 to 40° C.

2. The wearing article as defined by claim 1, wherein said fastening zones each comprises one of (i) said first adhesive layer and (ii) said plastic film strip; and
said landing zones each comprises the second adhesive layer.

3. The wearing article as defined by claim 2, wherein the second adhesive layer in each said landing zone is directly releasably bondable, in use, to the first adhesive layer of the corresponding fastening zone to releasably fasten the respective longitudinally extending side edges of said first and second waist regions together.

4. The wearing article as defined by claim 2, further comprising:
waist elastic members extending in a transverse direction of the article and contractibly attached to at least said transversely extending end of said second waist region;
leg elastic members extending in said longitudinal direction and contractibly attached to said crotch region along said longitudinally extending side edges thereof; and
a plurality of auxiliary elastic members spaced one from another in said longitudinal direction by a predetermined dimension, extending in said transverse direction, and contractibly attached to said article between said waist elastic members and said leg elastic members in at least said second waist region;
wherein
lengthwise ends of said waist elastic members, lengthwise ends of said leg elastic members and lengthwise ends of said auxiliary elastic members extend toward said longitudinally extending side edges of said second waist region where said lengthwise ends are interposed between said sheets and tightly bonded to said mutually opposed surfaces of said sheets.

5. The wearing article as defined by claim 4, wherein said lengthwise ends of said auxiliary elastic members terminate in a vicinity of mutually opposed inner side edges of said landing zones.

6. The wearing article as defined by claim 5, wherein said lengthwise ends of said waist elastic members as well as lengthwise ends of said leg elastic members terminate in the vicinity of said mutually opposed inner side edges of said landing zones.

7. The wearing article as defined by claim 2, wherein both said first adhesive layer and said second adhesive layer have a thickness dimension in a range of 5 to 100 μm.

8. The wearing article as defined by claim 2, wherein said second adhesive layer has a thickness dimension in a range of 5 to 100 μm.

9. The wearing article as defined by claim 7, wherein said sheets of each of the longitudinally extending side edges of said second waist region are tightly bonded so that, in use, the first adhesive layer is at the temperature of 36 to 40° C., due to the wearer's body warmth, one hour after said fastening zones have been directly, releasably bonded to said landing zones.

10. The wearing article as defined by claim 8, wherein said sheets of each of the longitudinally extending side edges of said second waist region are tightly bonded so that, in use, the first adhesive layer is at the temperature of 36 to 40° C., due to the wearer's body warmth, one hour after said fastening zones have been directly, releasably bonded to said landing zones.

11. The wearing article as defined by claim 4, wherein
 each of said landing zones is elongated in the longitudinal direction to extend from above the uppermost waist elastic member to below the lowermost elastic member, and overlaps the respective lengthwise ends of all said waist elastic members, auxiliary elastic members, and leg elastic members;
 each of said landing zones further comprises an outer side edge longitudinally extending along the respective longitudinally extending side edge of said second waist region and an inner side edge located inwardly of and opposite to the outer side edge in the transverse direction; and
 said lengthwise ends of all said auxiliary elastic members, waist elastic members and leg elastic members terminate in a vicinity of the respective inner side edges of said landing zones.

12. The wearing article as defined by claim 10, wherein
 each of said landing zones is elongated in the longitudinal direction to extend from above the uppermost waist elastic member to below the lowermost elastic member, and overlaps the respective lengthwise ends of all said waist elastic members, auxiliary elastic members, and leg elastic members;
 each of said landing zones further comprises an outer side edge longitudinally extending along the respective longitudinally extending side edge of said second waist region and an inner side edge located inwardly of and opposite to the outer side edge in the transverse direction; and
 said lengthwise ends of all said auxiliary elastic members, waist elastic members and leg elastic members terminate in a vicinity of the respective inner side edges of said landing zones.

13. The wearing article as defined by claim 2, wherein adhesive material of said second adhesive layer is one selected from the group consisting of acrylic adhesive, silicone adhesive and polyvinyl ether adhesive.

* * * * *